US006277078B1

(12) United States Patent
Porat et al.

(10) Patent No.: US 6,277,078 B1
(45) Date of Patent: Aug. 21, 2001

(54) SYSTEM AND METHOD FOR MONITORING A PARAMETER ASSOCIATED WITH THE PERFORMANCE OF A HEART

(75) Inventors: Yariv Porat, Haifa; Yoseph Rozenman; Abraham Penner, both of Tel-Aviv, all of (IL)

(73) Assignee: Remon Medical Technologies, Ltd., Caesarea (IL)

( * ) Notice: Subject to any disclaimer, the term of this patent is extended or adjusted under 35 U.S.C. 154(b) by 0 days.

(21) Appl. No.: 09/443,341

(22) Filed: Nov. 19, 1999

(51) Int. Cl.[7] ..................................................... A61B 5/00

(52) U.S. Cl. .......................... 600/486; 600/505; 607/18; 607/23

(58) Field of Search ....................... 607/18, 23; 600/486, 600/488, 505

(56) References Cited

U.S. PATENT DOCUMENTS

| 3,568,661 | 3/1971 | Franklin . |
| 3,757,770 | 9/1973 | Brayshaw et al. . |
| 4,127,110 | 11/1978 | Bullara . |

(List continued on next page.)

FOREIGN PATENT DOCUMENTS

| 0897690 | 2/1999 | (EP) . |
| WO 8303345 | 10/1983 | (WO) . |
| WO 97/01986 | 1/1997 | (WO) . |
| WO 97/33513 | 9/1997 | (WO) . |
| WO 97/47236 | 12/1997 | (WO) . |
| WO 98/26716 | 6/1998 | (WO) . |
| WO 98/29030 | 7/1998 | (WO) . |
| WO 99/26530 | 6/1999 | (WO) . |
| WO 99/59460 | 11/1999 | (WO) . |
| WO 00/16686 | 3/2000 | (WO) . |

OTHER PUBLICATIONS

E.R. Cosman et al. (Massachussetts, Apr. 1979) "A Telemetric Pressure Sensor for Ventricular Shunt Systems" Surgical Neurology, vol. 11, No.4, pp. 287–294.

Z. Tang et al (May 1995) "Data Transmission from an Implantable Biotelemeter by Load–Shift Keying Using Circuit Configuration Modulator" IEEE Transactions on Biomedical Engineering, vol. 42, No. 5, pp. 524–528.

Dipl.–Ing Torsten Eggers et al (Germany) "Implantable Telemetric Endosystem (ITES)" IMSAS Institut Fur Mikrosensoren–Aktuatoren Und–Systeme. 2 pp.

T. Chuter et al (Sweden, Jan. 1997) "Aneurysm Pressure following Endovascular Exclusion" Eur. J. Vasc. Endovasc. Surg. vol. 13, pp. 85–87.

Prof. Dr. Johannes Zacheja et al (Germany, Sep. 1996) "An Implantable Microsystem for Biomedical Applications" Micro System Technologies 96, pp. 717–722.

(List continued on next page.)

Primary Examiner—Robert L. Nasser

(57) ABSTRACT

An intrabody implantable system for long-term, real time monitoring of at least one parameter associated with heart performance. The system includes (a) a first sensor being implantable within a heart and being for collecting information pertaining to a pressure in a first cavity of the heart; (b) at least one additional sensor being implantable in an blood vessel supporting blood flow into or out of a second cavity of the heart, the at least one additional sensor being for collecting information pertaining to a pressure and a flow within the blood vessel; and (c) at least one device implantable in the body and being in data communication with the first sensor and the at least one additional sensor, the at least one device being for receiving the information pertaining to the pressure in the first cavity of the heart and the information pertaining to the pressure and the flow within the blood vessel and for relaying the information pertaining to the pressure in the first cavity of the heart and the information pertaining to the pressure and the flow within the blood vessel outside the body.

34 Claims, 11 Drawing Sheets

U.S. PATENT DOCUMENTS

| | | |
|---|---|---|
| 4,227,407 | 10/1980 | Drost . |
| 4,519,401 | 5/1985 | Ko et al. . |
| 4,541,431 | 9/1985 | Ibrahim et al. . |
| 4,593,703 | 6/1986 | Cosman . |
| 4,600,855 | 7/1986 | Strachan . |
| 4,653,508 | 3/1987 | Cosman . |
| 4,660,568 | 4/1987 | Cosman . |
| 4,676,255 | 6/1987 | Cosman . |
| 4,781,715 | 11/1988 | Wurzel . |
| 4,846,191 | 7/1989 | Brockway et al. . |
| 4,899,752 * | 2/1990 | Cohen ................................. 607/23 |
| 5,024,224 | 6/1991 | Engebretson . |
| 5,178,153 | 1/1993 | Einzig . |
| 5,213,098 * | 5/1993 | Bennett et al. .................. 607/23 |
| 5,289,821 | 3/1994 | Swartz . |
| 5,314,457 | 5/1994 | Jeutter et al. . |
| 5,411,551 | 5/1995 | Winston et al. . |
| 5,423,334 | 6/1995 | Jordan . |
| 5,476,488 | 12/1995 | Morgan et al. . |
| 5,535,752 * | 7/1996 | Halperin et al. ................. 600/486 |
| 5,562,714 | 10/1996 | Grevious . |
| 5,564,434 * | 10/1996 | Halperin et al. ................. 600/488 |
| 5,571,152 | 11/1996 | Chen et al. . |
| 5,628,782 | 5/1997 | Myers . |
| 5,704,352 | 1/1998 | Tremblay et al. . |
| 5,733,313 | 3/1998 | Barreras, Sr. et al. . |
| 5,735,887 | 4/1998 | Barreras, Sr. et al. . |
| 5,741,316 | 4/1998 | Chen et al. . |
| 5,807,258 | 9/1998 | Cimochowski et al. . |
| 5,832,924 | 11/1998 | Archibald et al. . |
| 5,833,603 | 11/1998 | Kovacs et al. . |
| 5,843,135 | 12/1998 | Weijand et al. . |
| 5,873,835 | 2/1999 | Hastings et al. . |
| 5,957,950 | 9/1999 | Mockros et al. . |
| 5,967,986 | 10/1999 | Cimochowski et al. . |
| 6,024,704 * | 2/2000 | Meador et al. .................. 600/486 |
| 6,053,873 | 4/2000 | Govari et al. . |
| 6,171,252 * | 1/2001 | Roberts .......................... 600/488 |

OTHER PUBLICATIONS

C. Hierold et al (Germany,1998) "Implantable Low Power Integrated Pressure Sensor System for Minimal Invasive Telemetric Patient Monitoring" IEEE, pp. 568–573.

Dr. Harmut Runge (Germany, May 1998) "Implanted blood pressure sensor reduces risk of infection for patients hospitalized for long–term observation" Siemens Press Release pp. 1–2.

Karl E. Richard et al (Germany, Jan. 1999) "First clinical results with a telemetric shunt–integrated ICP–sensor" Neurological Research vol. 21, pp. 117–120.

T.A. Cochran et al (1990) "Aortic Aneurysm Abdominal", Current Therapy in Adult Medicine, Fourth Edition.

G. W. H. Schurink et al (1998) "Late Endoleak after Endovascular Therapy for Abdominal Aortic Aneurysm" Eur. J. Vasc. Endovasc. Surg. vol. 17, pp. 448–450.

GH White et al (1997) "Endoleak Following Endoluminal Repair of AAA: Management Options and Patient Outcomes", J. Endovasc Surg. p. I–45.

S. K. Gupta et al (1999) "Use of a Piezoelectric Film Sensor for Monitoring Vascular Grafts" The American Journal of Surgery vol. 160, pp. 182–186.

* cited by examiner

SYSTEM AND METHOD FOR MONITORING A PARAMETER ASSOCIATED WITH THE PERFORMANCE OF A HEART

FIELD AND BACKGROUND OF THE INVENTION

The present invention relates to a system and method for monitoring of at least one parameter associated with the performance of a heart. More particularly, the present invention relates to a system of intrabody implantable sensors with which the performance of a heart can be monitored at any given time point along a prolonged time period.

Chronic heart failure (CHF) results from a deterioration in heart function and is characterized by patterns of hemodynamic, renal, neural and hormonal responses.

The physiological disturbances in congestive heart failure are complex, but a common feature is impairment in the performance of the heart as a pump.

Congestive heart failure is typically brought on by left ventricular dysfunction (LVD). LVD is a condition characterized by impairment in the function of the left ventricular muscle. As a result of this impairment, a reduced cardiac output (which is the product of heart rate multiplied by stroke volume), and an increase in filling pressure are experienced. Left ventricular dysfunction is typically brought on by diseases such as ischemic heart disease, hypertensive heart disease, valvular heart disease, cardiomyopathies and myocarditis. Right ventricular dysfunction (RVD), is a condition of the right ventricle of the heart which is similar to LVD. RVD is usually secondary to LVD, but occasionally can result from a pulmonary disease, valvular pulmonic stenosis, or direct damage to the right ventricular myocardium.

A range of compensatory mechanisms are activated in response to congestive heart failure, which mechanisms are aimed at correcting the reduced cardiac output. These include intrinsic cardiac mechanisms such as, muscle stretching (to increase contractile power), hypertrophy (increase in muscle mass), and a change in the shape of the ventricle. Additionally, a neuro-endocrine response is evoked, leading to an adrenergic increase in heart rate and contraction force, activation of the Renin-Angiotensin-Aldosterone-System (RAAS) which induces vasoconstriction, fluid retention, and redistribution of blood flow. While the neuro-endocrine response is compensatory, it tends to overload the cardiovascular system, leading to additional myocardial damage, and eventually congestive heart failure.

The diagnosis of CHF is achieved by a combination of non-invasive and invasive procedures. These procedures include physical examination, electrocardiogram (ECG), blood tests, chest radiography and echocardiography. Additional tests may be prescribed if needed to establish the presence of the disease and it's etiology.

Management of a CHF patient is often an enormous challenge to the treating physician. The compensatory mechanisms evoked by heart failure, make it necessary to provide treatment at a broad front, which typically requires the balancing of several potent drugs. At times this treatment is thwarted by the compensatory mechanisms, which recompensate for the presence of the medical treatment. Thus, the medical treatment of CHF is more of a "disease management" task than a "treatment", and in essence relies upon balancing the hemodynamic status of the patient in a state of compensation, such that the progression of CHF is kept to a minimum.

The management of CHF also includes non-medical intervention such as exercise to the extent tolerated, weight control, sodium restriction, and abstinence from smoking and alcohol.

The delicate balance between compensation and effective treatment is easily upset, even by seemingly benign factors, such as common medication (e.g., aspirin), physiological factors, excitement, or gradual progression of the disease. This may plunge the patient into a decompensation crisis, which requires immediate corrective action so as to prevent the deterioration of the patient's condition which, if left unchecked, can lead to death.

Central to disease management is constant patient monitoring. Presently, the most commonly used monitoring devices, monitor parameters which indirectly indicate the hemodynamic status of the patient. However, different hemodynamic situations, which require radically different corrective actions, may present similar clinical findings and as such a correct treatment regimen cannot always be prescribed by a physician. Monitoring of more direct hemodynamic measures requires more complex procedures, such as echocardiography or invasive methods. These procedures are usually employed only when a hemodynamic crisis has developed, or when trial and error treatment has failed to produce the desired results. An additional obstacle to proper patient management is the frequency of monitoring. A hemodynamic crisis may develop in a matter of hours or days. Alternatively, the patient may go through a phase where the hemodynamic parameters slowly change into a decompensatory state in which case monitoring over a long period of time is required in order to detect the onset of such a change.

There are various methods to measure heart performance and as such to detect CHF. These methods are categorized as non-invasive or invasive measurement methods.

Non-invasive measurement methods obtain information which relates indirectly to the performance of the cardiovascular system.

For example, measurements of lung partial oxygen pressure ($pO_2$) at exhale can be exercised to monitor the state of a patient. Such measurements are cheap to perform and are non-invasive by nature, but the results are not considered a valid measure of the cardiac status in CHF unless corroborated by another independent measurement. Another method to determine $pO_2$ relies upon the metabolic rate ratio (see, for example, U.S. Pat. Nos. 4,909,259 and 5,836,300). The concentrations of oxygen and carbon dioxide in the breath of the patient are measured. The data obtained by these measurements also includes the effects of cardiac output (CO), lung problems and various other metabolic parameters and, as such this method requires additional data to be accurate.

Attempts have also been made to derive the principal CO parameters from ECG waveforms using an experimental model which relates stroke volume with ECG electrical parameters (see, for example, U.S. Pat. Nos. 5,025,795 and 4,854,327). Although these methods can easily be applied to long-term disease management, the lack of data pertaining to the significance and validity of the experimental model and its dependence on stress, past cardiac events and other parameters is not provided and as such these methods cannot be considered accurate. Moreover, none of these methods can be used to determine with accuracy the left ventricle filling pressure which is a crucial parameter for proper patient management.

The condition of a CHF patient can also be assessed by the heart size. This can be accomplished non-invasively by either x-rays or by an echo-cardiography, although in both cases highly accurate readings cannot be collected.

U.S. Pat. No. 5,178,151 discloses a non-invasive heart function monitor which measures cardiac volumes from torso movements in two planes combined with ECG measurements. An elaborate model is used to extract these volumes from the data. A highly skilled staff is required to assess the results of this procedure.

U.S. Pat Nos. 5,469,859; 5,735,284 and 4,450,527 all describe a non-invasive bio-impedance devices which employ two to four thoracic or peripheral electrodes utilizable in determining a patient's cardio-respiratory parameters. Although this approach can be used for long term disease management due to its simplicity and non-invasiveness, it suffers from several drawbacks. For example, the results obtained depend on perfect electrical coupling to the body at precise locations. In addition, since the electrical path in the human tissue is complex and varies with the individual and his/her breath regimen, the method yields semi-accurate results which oftentimes have to be correlated to other measurement methods. Finally, due to its non-specificity, the obtained CHF related results may be contributed by other edemic processes (e.g., in the lungs).

Although non-invasive procedures can be used to asses the condition of a patient suffering from CHF, such procedures do not provide the level of accuracy which can be achieved by invasive methods. Invasive methods typically use wiring and catheters to extract information directly from the heart to be externally processed, but since these methods can be hazardous to the patient they can only be implemented for short-term monitoring procedures (hours to a few days) or during surgical procedures. Such invasive methods are generally utilized in New York Heart Association (NYHA) class III and IV patients.

Several parameters can be measured via invasive procedures in order to determine cardiac performance. These parameters include "cardiac output" (CO), the "left ventricular end diastolic pressure" (LVEDP), "left ventricular filling pressure" (LVFP), "aortic flow", (AF), "pulmonary arterial pressure" (PAP), "pulmonary arterial flow" (PAF), "myocardial contractility" (MC) and heart size. Cardiac output is defined as the volume of blood pumped by the heart in one minute, and is the product of stroke volume multiplied by the average pulse rate per minute. LVFP can be measured either in the left atrium when the atrial valve is open, (ending in the closing of the mitral valve at the LVEDP), or in the pulmonary arterial trunk using the "wedge" method. Myocardial contractility can be measured as the time derivative of the left ventricular pressure, measured at the isovolumic contraction phase of the systolic cycle. The ejection fraction, EF, which is the ratio of stroke volume to the end-diastole left ventricular volume is considered another index of systolic ventricular function.

LVEDP and LVP are difficult to measure directly. The left ventricular flow is remarkably different than that of the right ventricle, being oftentimes characterized by a turbulent flow. Blood emboli formed due to such an invasive procedure, can migrate to the brain via the carotid artery. Furthermore, due to hazards associated with such placement of a catheter, long-term positioning in the left ventricle (LV) or left atrium (LA) is not typically employed, and thus the possibility of long-term monitoring is significantly limited. Since non-invasive echo measurements of the heart size and contractility are not always considered sufficient, myocardial contractility (MC) and heart size data can only be efficiently acquired through invasive procedures attaching position and acceleration sensors to the myocardium, or by using a pressure catheter inside the LV.

One invasive measurement method of CO requires the patient to breath pure $O_2$ from a spirometer with a $CO_2$ absorbr, while measuring the $O_2$ uptake directly from the net gas flux. Two catheters, one in the pulmonary artery (PA) and one in the brachial or frmoral artery are used to simple the mixed bloodstream. While theoretically this method can achieve a high degree of accuracy, this technique suffers from several inheret limitations which limit it's accuracy and efficiency. The patient cardiac output and $O_2$ consumption must be constant over several minutes for an accurate measurement to be taken; more than one catheter is required to effect measurements, which increases the risk of infection; a significant volume of blood is used by the test, rendering it inconvenient for repeated measurements, especially on infants or acutely ill patients; and, the monitors used to analyze gas concentration are often bulky, and/or located remote from the patient, making real-time analysis difficult or impossible. U.S. Pat. No. 5,040,538 to Mortazavi discloses a method which is a modem and invasive variant to $pO_2$ blood measurements. According to this method, $pO_2$ is measured using an optical sensor installed on the sensor side of a pacemaker catheter in the right atrium or ventricle. Oxygenation level is measured using a dual-LED sensor. A first LED illuminates the bloodstream while a second LED senses the reflected light from the blood, thus setting a pre-calibrated level of oxygen. The disclosed sensor output is sufficient to control the rate of a pacemaker, but may not be adequate for CO determination since the sensor level determination is not related in any form to $O_2$ consumption.

Of all the measurable hemodynamic parameters, LVEDP is considered the most valid and informative. Since a direct measurement of LVEDP is considered very risky, a wedge-pressure, which is typically acquired via a Swan-Ganz (SG) catheter, is often obtained as a representative parameter to LVEDP. Preferably, the catheter is introduced through a central vein, into the right atrium. It is maneuvered into the right ventricle and into the PA and positioned at the PA trunk. A balloon is inflated to block the flow in one of the PA branches, and the "wedge" pressure is taken at its distal end. The assumption is that since the blood flow is blocked, this value is equilibrated with and equals to the LA pressure, which in turn is equal to LVFP. A flow measurement is then taken by thermodilution in the PA trunk. The pressure and the flow are very close to their instantaneous values and waveforms in the LA. Although SG catheterization is not considered risky, a migration of the catheter into the branch of the PA may cause a pulmonary infarct. SG is, therefore, a proper tool only for acute CHF and cannot be used for extended disease management. Another approach which is described in U.S. Pat. No. 5,755,766 is to implant a pressure sensor in the great coronary vein situated on the myocardium, posterior to the LV, and measure approximate waveforms of the LVP.

A variation on the SG pressure and flow measurement, which utilizes an SG catheter, is the thermodilution method. In this method, the SG catheter is inserted, and a small prescribed volume of solution, which is colder than the blood, is instantaneously injected into the RA. Simultaneously, temperature versus time is measured at the PA downstream. Since both volume and temperature of the diluting sample, as well as the patient temperature are known, it is possible to obtain the flow values in terms of volume (see, for example, U.S. Pat. No. 5,277,191). U.S. Pat. No. 5,509,424 describes another device and method equivalent to the original SG catheter, but using a heated instead of a cooled sample. A mildly invasive method used to measure flow speed is Trans-esophageal echocardiography, (TEE) (see for example U.S. Pat. Nos. 5,052,395 and 5,022,410). An ultrasonic catheter is introduced through the esophagus down to the region of the descending aorta. Since the ascending aorta and the esophagus run almost parallel to each other, Doppler echo measurement of the flow speed in the aorta are difficult to obtain. Although the procedure is only mildly invasive, it is lengthy, cumbersome, expensive, unpleasant, and is usually performed in a hospital. In addition, the quality of the results is highly dependent on the operator skills. The method is, therefore, not appropriate for extended CHF management.

There is thus a widely recognized need for, and it would be highly advantageous to have, a measurement method which can be used to monitor hemodynamic parameters of a CHF patient over an extended period of time. Such a method enables to determine the hemodynamic status of a patient and therefor will enable optimizing a suitable therapy regimen accordingly. Using such method, disease management of for example, NYHA type III and type IV patients would be greatly simplified thus helping improve life expectancy in such individuals.

SUMMARY OF THE INVENTION

According to one aspect of the present invention there is provided an intrabody implantable system for long-term, real time monitoring of at least one parameter associated with heart performance, the system comprising (a) a first sensor being implantable within a heart and being for collecting information pertaining to a pressure in a first cavity of the heart; (b) at least one additional sensor being implantable in an blood vessel supporting blood flow into or out of a second cavity of the heart, the at least one additional sensor being for collecting information pertaining to a pressure and a flow within the blood vessel; and (c) at least one device implantable in the body and being in data communication with the first sensor and the at least one additional sensor, the at least one device being for receiving the information pertaining to the pressure in the first cavity of the heart and the information pertaining to the pressure and the flow within the blood vessel and for relaying the information pertaining to the pressure in the first cavity of the heart and the information pertaining to the pressure and the flow within the blood vessel outside the body.

According to further features in preferred embodiments of the invention described below, the first cavity is a ventricle.

According to still further features in the described preferred embodiments the blood vessel is an artery.

According to still further features in the described preferred embodiments the artery is a pulmonary artery.

According to still further features in the described preferred embodiments the at least one additional sensor includes at least two pressure sensors being implantable in a spaced apart configuration within the blood vessel, the at least two pressure sensors being for collecting the information pertaining to the pressure and the flow within the blood vessel.

According to still further features in the described preferred embodiments the system further comprising an extracorporeal processing unit capable of receiving, processing and interpreting the information pertaining to the pressure in the a first cavity of the heart and the information pertaining to the pressure and the flow within the blood vessel relayed outside the body by the at least one device.

According to still further features in the described preferred embodiments the first sensor is a pressure sensor and further wherein the information pertaining to the pressure in the a first cavity of the heart pertains to both active and passive pressures within the a first cavity.

According to still further features in the described preferred embodiments the at least one device includes at least one transducer for converting electric signal into a radiative signal.

According to still further features in the described preferred embodiments the radiative signal is selected from the group consisting of radio frequency, a magnetic field, an electric field and acoustic radiation.

According to still further features in the described preferred embodiments the at least one transducer is an acoustic transducer and further wherein the radiative signal is an acoustic signal.

According to still further features in the described preferred embodiments the transducer is a magnetic field transducer and further wherein the signal is a magnetic field signal.

According to still further features in the described preferred embodiments the system further comprising at least one power source, the at least one power source being in electrical communication with the first sensor and the at least one additional sensor.

According to still further features in the described preferred embodiments the at least one power source is integrated into the at least one device.

According to still further features in the described preferred embodiments the at least one power source is selected from the group consisting of at least one energy containing power source and at least one energizeable power source.

According to still further features in the described preferred embodiments the at least one energizeable power source includes at least one transducer for converting a radiative energy into electric energy.

According to still further features in the described preferred embodiments the radiative energy is selected from the group consisting of radio frequency, a magnetic field, an electric field and acoustic radiation.

According to still further features in the described preferred embodiments the at least one transducer is an acoustic transducer and further wherein the radiative energy is an acoustic energy.

According to still further features in the described preferred embodiments the transducer is a magnetic field transducer and further wherein the radiative energy is a magnetic field.

According to still further features in the described preferred embodiments the at least additional sensor is attached to or integrally formed with a stent assembly, the stent assembly being configured so as to be positionable within the blood vessel.

According to still further features in the described preferred embodiments the at least one device includes a plurality of devices and further wherein the stent assembly includes a device of the plurality of devices attached thereto and being in communication with the at least one additional sensor.

According to still further features in the described preferred embodiments the at least two pressure sensors are attached to or integrally formed with a stent assembly, the stent assembly being configured so as to be positionable within the blood vessel.

According to still further features in the described preferred embodiments the at least one device includes a plurality of devices and further wherein the stent assembly includes a device of the plurality of devices attached thereto and being in communication with each of the at least two pressure sensors.

According to another aspect of the present invention there is provided a method of monitoring the heart performance of an individual, the method comprising the steps of (a) implanting within the patient's body (i) a first sensor being implantable within a heart and being for collecting information pertaining to a pressure in a first cavity of the heart; and (ii) at least one additional sensor being implantable in an blood vessel supporting blood flow into or out of a second cavity of the heart, the at least one additional sensor being for collecting information pertaining to a pressure and a flow within the blood vessel; (b) extracorporeally retrieving and processing the information collected by the first sensor and the information collected by the at least one additional sensor; (c) interpreting the information resultant from step (b) so as to yield interpreted information pertaining to the heart performance of the patient; and (d) if required, repeating steps (b) through (c) a predetermined number of times over a predetermined time period so as to enable monitoring the heart performance of the individual.

According to further features in preferred embodiments of the invention described below, the information pertaining to a pressure in the a first cavity of the heart pertains to both active and passive pressures within the a first cavity.

According to still further features in the described preferred embodiments the at least one additional sensor includes at least two pressure sensors being implantable in a spaced apart configuration within the blood vessel, the at least two pressure sensors being for collecting the information pertaining to the pressure and the flow within the blood vessel.

According to still further features in the described preferred embodiments the first sensor is a pressure sensor and further wherein the information pertaining to the pressure in the a first cavity of the heart pertains to both active and passive pressures within the a first cavity.

According to still further features in the described preferred embodiments the at least additional sensor is attached to or integrally formed with a stent assembly, the stent assembly being configured so as to be positionable within the blood vessel.

According to still further features in the described preferred embodiments the step of extracorporeally retrieving and processing the information collected by the first sensor and the information collected by the at least one additional sensor is effected by an extracorporeal processing unit being in communication with the first sensor and the at least one additional sensor.

According to still further features in the described preferred embodiments the communication is selected from the group consisting of wire communication and wireless communication.

According to still further features in the described preferred embodiments the wireless communication is effected via radiative energy selected from the group consisting of radiofrequency energy, acoustic energy and magnetic field energy.

According to yet another aspect of the present invention there is provided a method of monitoring the heart performance of an individual, the method comprising the steps of (a) collecting and processing information pertaining to a pressure in a cavity of the heart; (b) collecting and processing information pertaining to a pressure and a flow within an blood vessel supporting blood flow into or out of the heart; (c) interpreting the information resultant from step (b) and the information resultant from step (c) so as to yield interpreted information pertaining to the heart performance of the patient; and (d) repeating steps (b)–(d) a predetermined number of times over a predetermined time period so as to enable monitoring the heart performance of the individual.

The present invention successfully addresses the shortcomings of the presently known configurations by providing a system of intrabody implantable sensors with which the performance of a heart can be monitored at any given time point along a prolonged time period.

Implementation of the method and system of the present invention involves performing or completing selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1A:
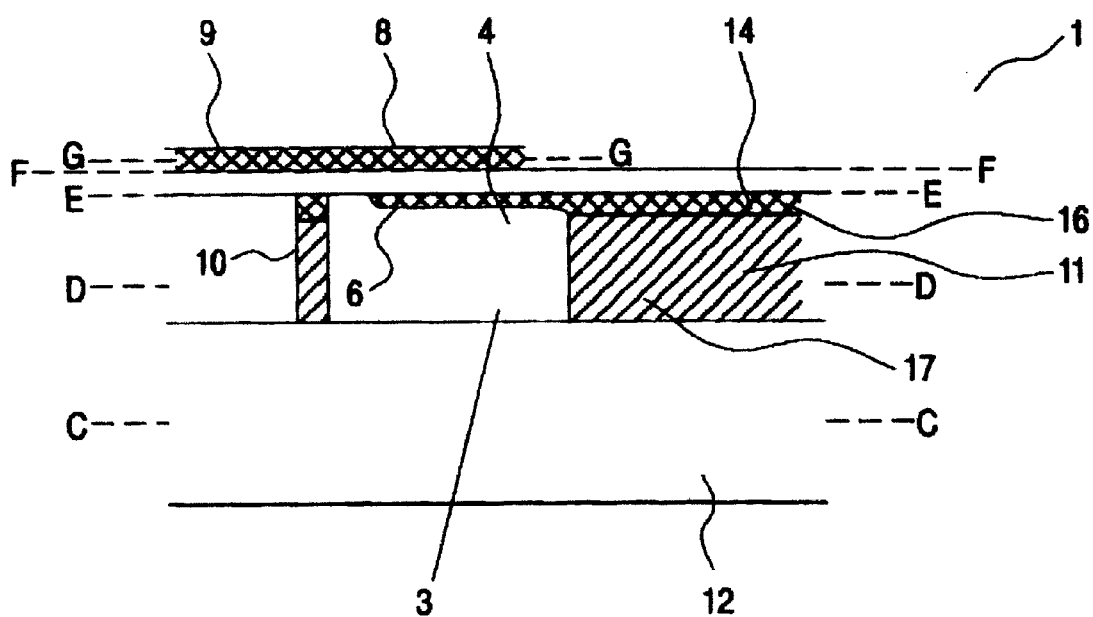
FIG. 1a is a longitudinal section of a transducer element according to the present invention taken along lines A—A in FIGS. 2a–2e (prior art, described in PCT/US98/27669)

The present invention is of a system and method which can be used to monitor heart performance of an individual. Specifically, the present invention utilizes a plurality of intrabody implantable sensors for monitoring the active and passive pressures of a heart chamber such as, for example, the left ventricle, and the pressure and flow in an artery supporting blood flow from the heart, so as to enable to determine the performance of the heart at any given time point over an extended period of time.

The principles and operation of a system and method according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Referring now to the drawings, FIGS. 10–14 illustrate the system for long-term, real time monitoring of at least one parameter associated with heart performance according to the present invention, which is referred to hereinunder as system 100.

Figure 10:
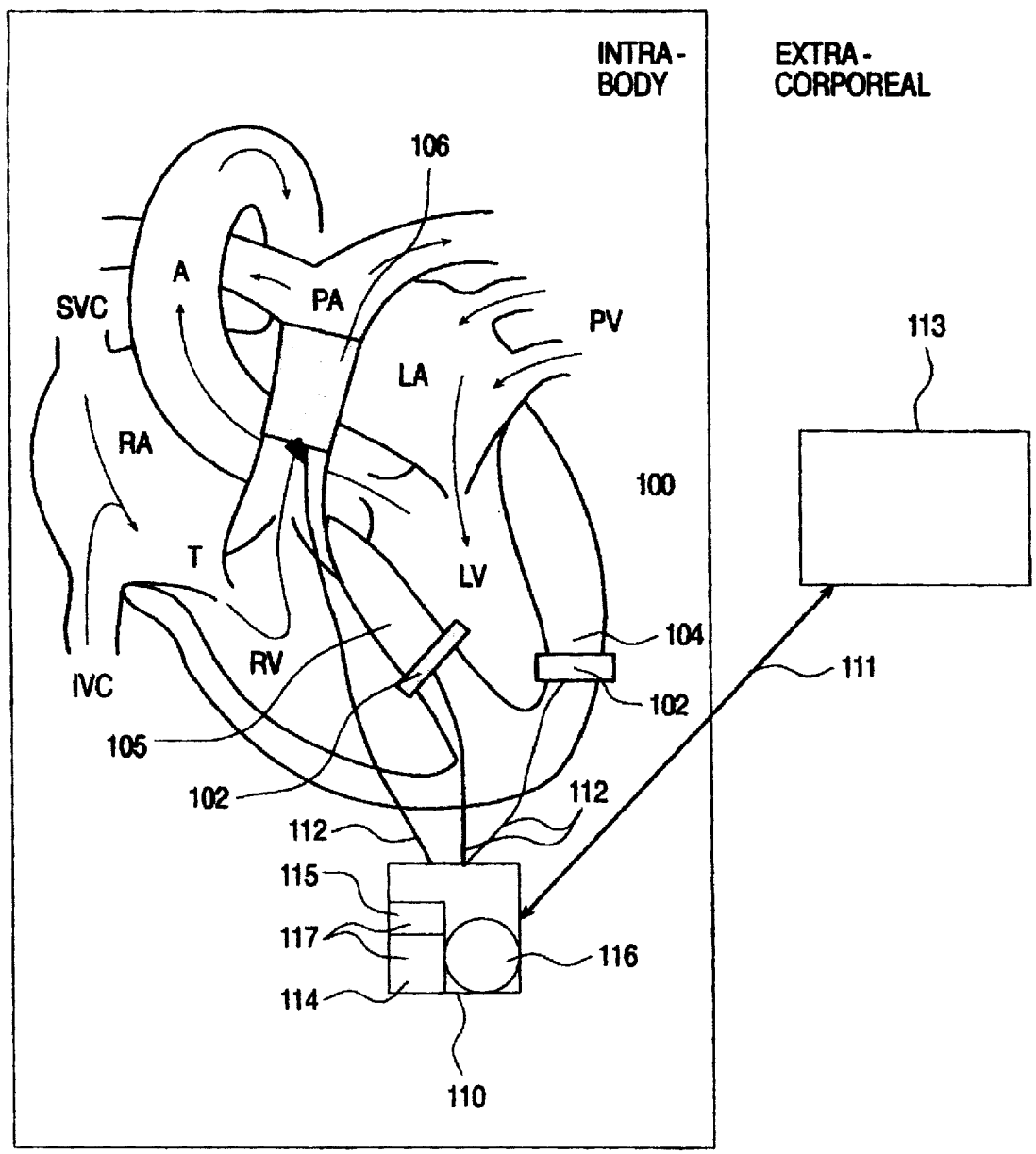
FIG. 10 is a schematic depiction presenting the intra-body and extracorporeal positioning of the various components of one embodiment of the system of the present invention; PA—pulmonary artery, A—aorta, PV—pulmonary vein, SVC—superior vena cava, IVC—inferior vena cava, RA—right atrium, RV—right ventricle, LA—left atrium, LV—left ventricle.

System 100 includes a first sensor 102 which is implantable within a heart and which serves for collecting information pertaining to a pressure in a chamber (i.e., a cavity, either a ventricle or an atrium) of the heart, preferably a ventricle, more preferably a left ventricle. As is shown in FIG. 10, sensor 102 can be implanted, for example, in either a septum 103 or the myocardium 104 surrounding the left ventricle. Alternatively a plurality of sensors 102 can be utilized, each implanted in a different region surrounding the left ventricle. In any case, sensor 102 is implanted so as to protrude into the left ventricular cavity, thus enabling the direct collection of information pertaining to the pressure in the left ventricle of the heart. This information includes both the active and passive left ventricular pressures measurable during a complete heart cycle.

It will be appreciated that although left ventricular placement of sensor 102 is most preferred, sensor 102 can also be implanted within the right ventricle or alternatively an atrium in which case information pertaining to a pressure in the right ventricle or an atrium of the heart can be collected thereby. Although pressure information from the right ventricle or an atrium is not considered as reliable as pressure information from the left ventricle when utilized for the determination of heart performance, such information can still be utilized as a parameter by the present invention to determine such performance.

System 100 also includes at least one additional sensor 106. Sensor(s) 106 is implantable in a blood vessel supporting blood flow into or out of the heart. Preferably sensor(s) 106 are implanted within an artery. Sensor 106 serves for collecting information pertaining to a pressure and a flow within that artery. According to a preferred embodiment of the present invention, sensor 106 is implanted in the pulmonary artery. It will be appreciate that sensor(s) 106 can also be implanted in the aorta, although pressure readings from this artery can be unreliable due to pressure fluctuations and irregular blood flow therein. It will further be appreciate that sensor(s) 106 can also be implanted in veins supporting blood flow into a heart cavity although pressure and flow information from these vessels is considered less reliable and informative.

It will be appreciated that sensors 102 and 106 must be securely anchored to the tissue into which they are implanted since unwanted dislodgment and separation from the tissue can lead to blood vessel blockage and/or damage which can pose a serious health hazard to the individual. As such, sensors 102 and 106 are preferably provided with various anchoring mechanisms including, but not limited to, various stud and screw configurations, such that when implanted within the tissue, no accidental dislodgment of these sensors occurs. Of particular interest are studs having a deployable anchoring system. Methods of anchoring intrabody fixtures are well known in the art and are therefore not further described herein.

To effect pressure and flow measurements, sensor(s) 106 can function as a combination flow and pressure sensor such as for example AM5103-008-G distributed by Analog Microelectronics (http://www.analogmicro.de). Alternatively, sensor 106 can be part of an assembly which includes a pressure sensor and a flow sensor both of which are integrated into a single housing (see for example, U.S. Pat. No. 5,833,603).

Figure 11:
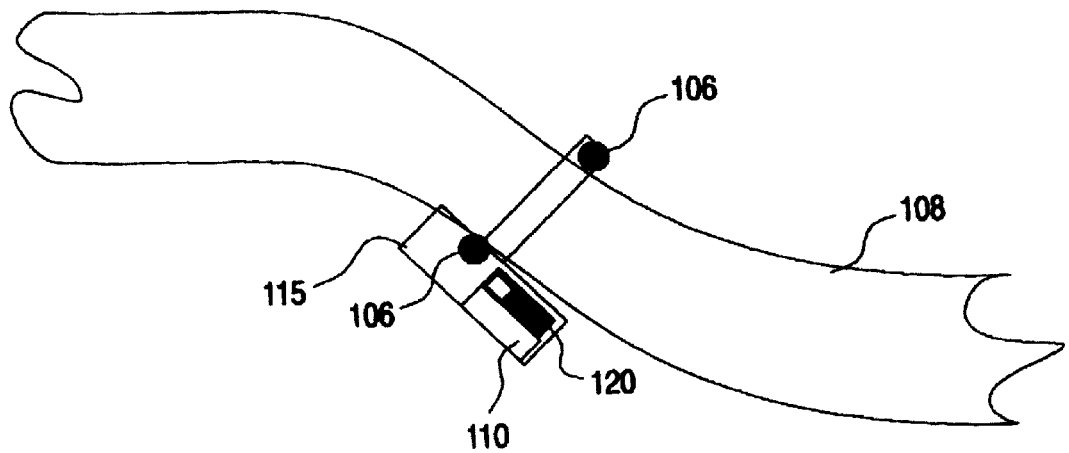
FIG. 11 is a schematic depiction of one embodiment of an arterial pressure and flow sensor assembly according to the present invention.
Figure 12:
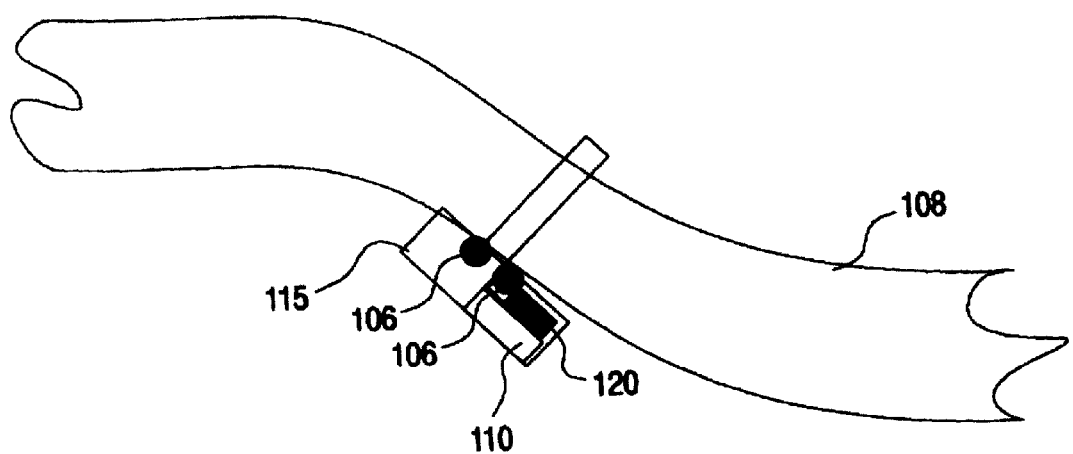
FIG. 12 is a schematic depiction of another embodiment of an arterial pressure and flow sensor assembly according to the present invention.

Still alternatively, as shown in FIGS. 11 and 12 and according to another preferred embodiment of the present invention, sensor(s) 106 5 includes two pressure sensors which are implantable in a spaced apart configuration either on the same inner wall (FIG. 12) or on opposing inner walls (FIG. 11) of a pulmonary artery 108. In any case, sensors 106 are positioned in different positions along a length of artery 108 and as such measure pressures along a length of artery 108 delimited thereby. Sensors 106 serve for collecting information pertaining to pressure and flow within the artery. By measuring pressures at points along the length of artery 108 a pulsatile flow rate can be determined. Example 1 of the Examples section which follows describes in detail a method of extracting pulsatile flow rates of fluid in a pipe from two adjacently positioned pressure sensors.

Figure 13:
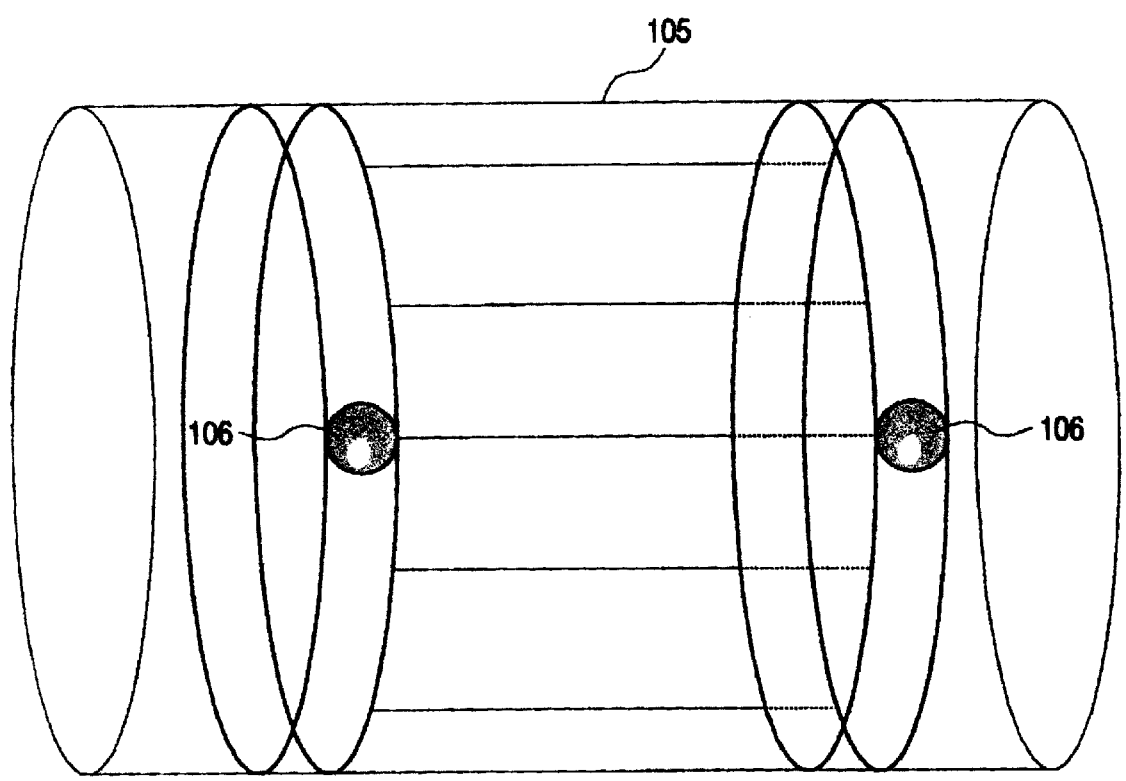
FIG. 13 is a schematic depiction of an artery positionable stent assembly including sensors useful for measuring flow and pressure within the artery according to the present invention.

According to another preferred embodiment of the present invention and as is specifically shown in FIGS. 11–13 sensors 106 are integrally formed with or attached to a stent 105. Stent 105 is configured so as to be positionable within artery 108, using conventional stent deployment techniques. It will be appreciated that any assembly which can be used to position sensors 106 within an artery can be utilized by the present invention.

In order to calculate the performance of the heart information collected from sensors 102 and 106 must be provided outside the body.

As such, as shown in FIG. 10, system 100 further includes at least one data relaying device 110. Device 110 is implantable within the body in a region proximal to the heart or on the heart tissue. Device 110 is in data communication with sensor 102 and with sensor(s) 106 via electrical wire connections (indicated by 112). Device 110 serves for receiving information from sensors 102 and 106 and relaying this information outside the body.

As such, and according to one embodiment of the present invention device 110 includes wires which extend out of the body and which serve for electrically relaying the information out of the body as an electrical signal.

Alternatively and presently preferably device 110 includes a transmitter which serves for transmitting this information outside the body as either a radiofrequency, acoustic, magnetic field or electric field signals. Thus, a transmitter 114 incorporated in device 110 can be either a radiofrequency transmitter, an acoustic transmitter, a magnetic field transmitter or an electric field transmitter. Further description to such transmitter types is given hereinbelow in context with the transducer embodiments.

It will be appreciated that sensors 102 and 106 can be configured to automatically collect information periodically such that this information is in turn periodically transmitted by device 110 outside the body.

Preferably sensors 102 and 106 are configured such that collection of information thereby is prompted upon reception of a prompting signal from device 110. It will be appreciated that since device 110 receives information from sensors 102 and 106, these sensors are each configured such that the information relayed therefrom is coded or modulated so as to be each specifically and independently recognizable by device 110. Alternatively, device 110 is configured such that each of sensors 102 and 106 is commanded to operate at a different time point. In any case, the signal relayed outside the body by device 110 is modulated over one or more frequencies and/or time such that the information from sensors 102 and 106 can be processed separately outside the body.

Alternatively, device 110 can be configured to both digitize and modulate the information collected by sensors 102 and 106 so that the signal relayed outside the body is in digital format and that each sensor information is recognizable by a different carrier frequency.

Device 110 can be configured so as to automatically issue a prompting signal at predetermined time points. Alternatively and preferably device 110 receives a command signal from outside the body and relays the prompting signal to sensors 102 and 106.

It will be appreciated that above mentioned tasks which include retrieval and modulation of sensor collected information and interpretation of a command signal are preferably handled by a microprocessor which is included within device 110. Numerous examples of microprocessors which can be utilized by device 110 are known in the art and as such no further detail of such microprocessors is given herein.

To enable reception of signals from outside the body, device 110 also includes a receiver 115. Receiver 115 serves for receiving command signals from outside the body, which command signals switch on sensors 102 and 106. Receiver 115 is similar in type to transmitter 114 described above. Preferably receiver 115 and transmitter 114 are integrated into a transceiver 117 capable of both receiving and transmitting signals of various types.

According to another preferred embodiment of the present invention, system 100 further includes an extracorporeal processing unit 113 which serves to collect information relayed by device 110. Extracorporeal processing unit communicates with device 110 through either wire or wireless communication modes (indicated by 111) depending on the configuration of device 110.

According to another preferred embodiment of the present invention system 100 includes at least one power source 116 which is also implantable within the body. Preferably, and as shown in FIG. 10, power source 116 is integrated into device 110. Power source 116 serves to provide power to all the necessary functions of system 100. Thus power source communicates a power signal to sensors 102 and 106 and to transmitter 114.

Power source 116 can be an energy containing power source such as, but not limited to, a battery or alternatively and preferably an energizeable power source, such as, but not limited to, a capacitor or a transducer.

Figure 14:
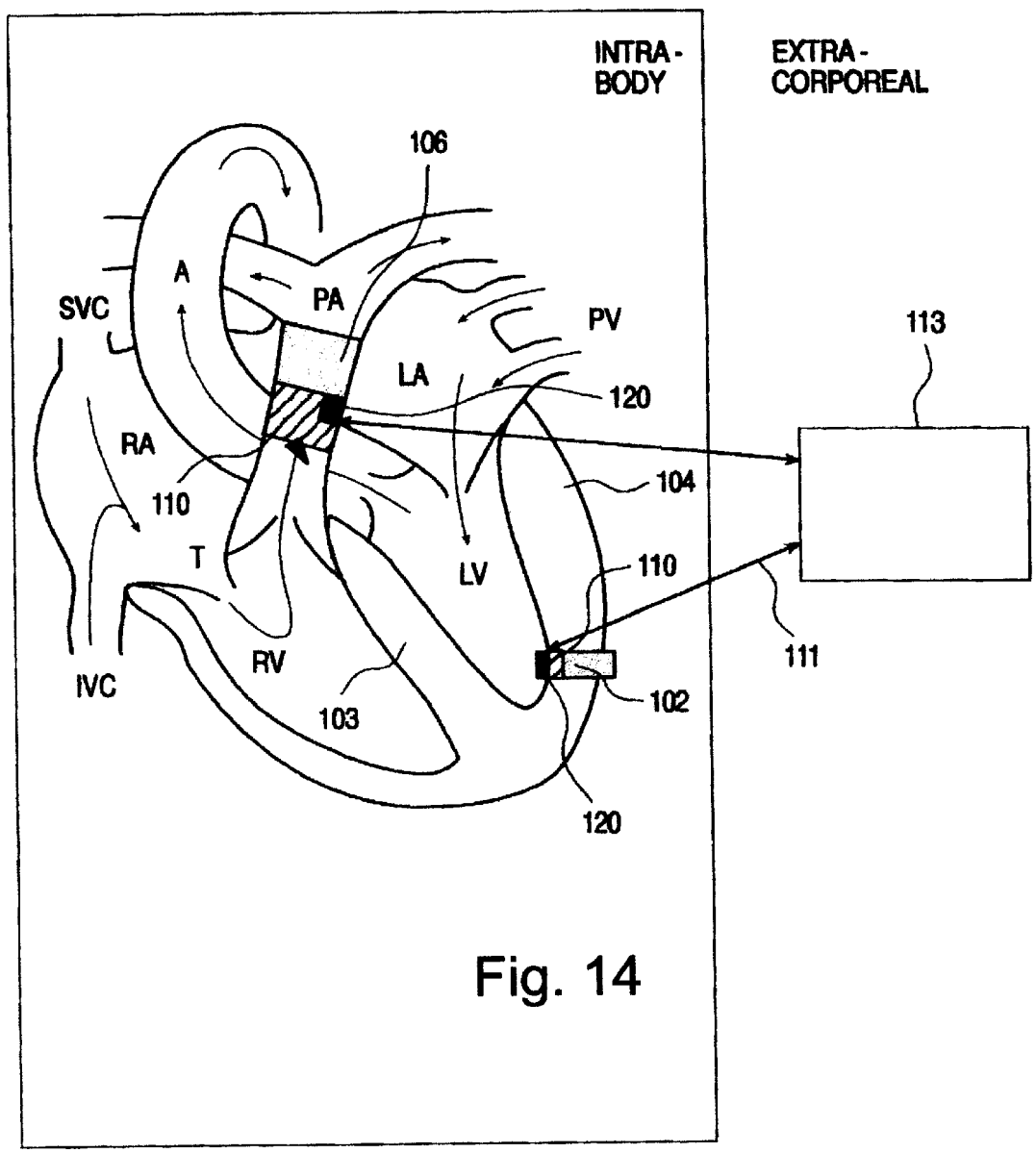
FIG. 14 is a schematic depiction presenting the intra-body and extracorporeal positioning of the various components of another embodiment of the system of the present invention; PA—pulmonary artery, A—aorta, PV—pulmonary vein, SVC—superior vena cava, IVC—inferior vena cava, RA—right atrium, RV—right ventricle, LA—left atrium, LV—left ventricle.

According to a presently preferred embodiment of the present invention and as specifically shown in FIG. 14, an independent device 110 is integrated into sensor 102 and each of sensors 106. According to this configuration the function of both power source 116 and transceiver 117 are preferably handled by a transducer or transducers 120. Thus, each transducer 120 of a device 110 serves to both supply sensors 102 and 106 with power and for transmitting and receiving signals.

As is specifically shown in FIGS. 11 and 12, when sensors 106 are integrated into stent 105, a single device 110, which is integrated or attached to stent 105 can be employed to provide power to, and communication to and from, sensors 106.

According to a preferred embodiment of the present invention transducer 120 can receive and transmit radiative energy such as, but not limited to, radio frequency radiative energy, a magnetic field radiative energy, an electric field radiative energy and acoustic radiation radiative energy. In any case, transducer 120 can convert radiative energy impinging thereupon into electrical energy which can be used to power sensors 102 and 106, and convert electrical energy received thereby from sensors 102 and 106 into transmitted radiative energy which is receivable outside the body.

According to one preferred embodiment of the present invention, transducer 120 is a magnetic field transducer. As such transducer 120 can include, for example, multiturn wire coils, coils implemented in a very large scale integration (VLSI) silicon devices, a Hall effect detector, a coupled split-drain field effect transistor (MAGFET) device, and a magnetoresistive field effect transistor (FET) detector. Preferably, transducer 120 uses at least three mutually orthogonal electromagnetic multiturn wire coils or any of the similar functioning elements mentioned above, such that a magnetic field can be detected (received) from at least three planes. Magnetic field transducers which convert a magnetic field to an electrical current and vice versa are well known in the art. For further detail, see, for example, U.S. Pat. Nos. 4,845,503; 5,729,129 and 5,558,091 which are incorporated herein by reference.

According to another preferred embodiment of the present invention transducer 120 is a radiofrequency transducer designed to receive and transmit signal within the radiofrequency range.

According to a preferred embodiment of the present invention radio frequency transducer 120 employs Lumped-Constant (L-C) circuits. Transducers incorporating L-C circuits are well known in the art and therefore require no further description herein. For example, U.S. Pat. Nos. 3,943,915 and 4,593,703, which are incorporated herein by reference, teach transducers incorporating L-C circuits which are employed to relay information from an intracranial pressure sensor outside the body of the patient.

According to a presently preferred embodiment of the present invention, transducer 120 is an acoustic transducer. The use of an acoustic transducer 120 is particularly advantageous since acoustic signals travel efficiently through a water containing body such as a human body.

The operation of acoustic transducers is described in detail in U.S. patent application Ser. No. 09/000,553 and PCT/US98/27669 which are incorporated herein by reference and further in Example 2 of the Examples section that follows.

For system 100 to function properly and efficiently, the implanted transceiver and the power source thereof, which can include acoustic, radiofrequency, magnetic field or electric field transducers, must be miniature in size and produce the power necessary for the various functions thereof from the impinging energy.

The current consumed by magnetic field transducers depends on their structure. Magnetic pickup coils do not require any current to operate, rather they produce current in response to an energizing magnetic field. The only power requirement comes from the amplifiers. Using FET input stages, a power requirement of an amplification stage can be 5 $\mu$W or less. MAGFET and Hall effect transducers also require extremely low power in order to operate, due to the high input impedance of FET devices.

Power is also consumed by sensors 102 and 106 and by transceiver 117, which receives and transmits signals. A receiving/transmitting transducer can also double as an efficient power converter. When the converter is an acoustical converter, and operated at its mechanical resonance, it is an efficient power conversion system.

The above electrical power requirements can be easily satisfied by for example acoustic transducer which can convert acoustic energy to an electric energy. A single transducer cell, of the type described in the Examples section, has a diameter of around 1 mm and thickness of roughly 0.15 mm. Such a cell can be made to yield 100–200 $\mu$W of electrical energy for a surface area of 0.8 mm$^2$.

Thus, in order to supply the energy requirements of system 100 and yet retain the smallest size possible a preferable configuration of system 100 includes acoustic transducers doubling as both power energy converters and transceivers.

As such, sufficient power to energize system 100 can be acquired from a few acoustic transducers. To this end, a possible sensor and device 110 assembly could be for example, a cylindrical structure 2–3 mm in diameter and 3–5 mm in length. Such a structure can easily include both device 110 and the sensor(s) communicating thereto. Such a device is small enough to be implantable in a minimally invasive manner via a standard biopsy needle or a stent guide.

Thus, system 100 of the present invention can be used to monitor a performance parameter associated with the heart as follows.

In a first step, any of the above mentioned embodiments of the intrabody portion of system 100 (sensors 102 and 106 and device(s) 110) are implanted within a body of an individual. Following which, and in the case of an energy containing power source 116 embodiment of system 100, a signal is transmitted from extracorporeal processing unit 113 to device 110, which signal commands sensors 102 and 106 to collect information. Alternatively, when an energizeable power source 116 is utilized by system 100, such a signal is converted by transducer(s) 120 of device 110 into power for powering sensors 102 and 106 to switch on and collect information. It will be appreciated that sensors 102 and 106 are supplied with power from power source 116 for a time period which is sufficiently long so as to enable the collection of information thereby and the communication thereof to device. For example, since sensor 102 preferably collects both active and passive pressures from the left ventricle, sensor 102 needs to be powered for a time period covering preferably a single heart beat or at least the steep ascent of the diastole portion of the heart beat.

Following collection of the information from sensors 102 and 106, device 110 transmits a signal or signal receivable by extracorporeal unit 113, which signal pertains to the information collected by sensors 102 and 106.

The signal is then processed and interpreted by extracorporeal processing unit 113 so as to yield information pertaining to the heart performance of the patient at a specific time point. Such retrieval and interpretation of information can be effected at various time points such that the heart performance of an individual can be monitored over an extended period of time.

The information retrieved and interpreted by extracorporeal processing unit 113 can be used to generate a value for at least one parameter with which the performance of the heart can be assessed and monitored. When system 100 is utilized in it's preferred configuration in which sensor 102 is implanted in the left ventricle and sensors 106 are implanted in the pulmonary artery such parameters can be, but are not limited to, left ventricular pressure (LVP), myocardial contractility (MC), left ventricle end diastolic pressure (LVEDP) and pulmonary artery pressure (PAP) which values are indicative of the performance of the heart.

These parameter values can further be used to generate additional parameter values relating to the stroke volume of the heart and to the relative efficiency of the heart in pumping blood (represented by MC or EFR).

It will be appreciated that obtaining parameter values by monitoring either the pressure in the left ventricle or the pressure and flow in an artery exiting the heart is well known in the art. To this effect the reader is referred to Cardiovascular Fluid Dynamics, ASIN 0849355737, by Uri Dinnar CRC Press, Inc., Boca Raton, Fla., USA, 1981, chapters 54, 56 and 57, which is incorporated herein by reference).

Thus, according to the present invention the parameter values obtained from the implanted sensor configurations of the system of the present invention can yield several hemodynamic parameters such as pressures, volumes, velocities, accelerations, and flow which can be used to assess the performance of a heart.

Some of the parameters are directly derived from the primary measurements effected by the implanted sensor configurations of the system of the present invention, and some are deduced from the primary measurements using simple mathematical operations.

In the present invention a value corresponding to the left ventricular pressure (LVP) of the heart is obtained by implanting a pressure sensor within the left ventricle (LV) either through the myocardium or the septum.

The left ventricular pressure, represents the capacity of the left half of the heart, especially the left ventricle, throughout the full cardiac cycle. It is important for the physician to be able to follow the peak systole pressure, and its rate of increase with time. The rate of increase in the steepest part of the ascent is a measure of myocardial contractility (MC). The actual calculation involves finding the time slope of the LVP during its isovolumetric contraction. Similarly, the negative of the LV pressure over time in the isovolumetric relaxation is a good measure of the diastolic function The mean pulmonary arterial pressure (PAP) of a healthy individual is typically 5 mm Hg higher than the left ventricular pressure. This is due to the pulmonary vascular resistance. Nevertheless, in the rare cases of pulmonary disease, this pressure difference can be as much as 30 mm Hg higher than the value in a healthy individual. Detection of such abnormal pulmonary arterial pressure can be indicative of various cardiac diseases.

The present invention enables calculating the pulmonary arterial velocity from pressure gradient measurements. PAF (Pulmonary Arterial Pressure) is obtained by multiplying the integrated velocity over one heart cycle by the cross-sectional area of the pulmonary artery (PA). The value of this parameter integrated over one minute yields the Cardiac Output (CO), which is indicative of the volume of blood supplied by the heart to the body.

Since information from the left ventricle and the pulmonary artery is retrieved according to the present invention at the same time it is possible to correlate between a measured hemodynamic parameter attributable to the left half of the heart and a hemodynamic parameter measured in the right half of the heart simultaneously. For example, PAP and LVP can yield, when correlated over several simultaneous measurements, information related to a heart condition which is generated by both left and right heart dysfunctions.

In any case, it will be appreciated that the heart performance parameters obtainable directly or indirectly by the present invention as described above can be either correlated to parameters obtained from other measurement methods such as for example an electrocardiogram (ECG) or it can be correlated to similar information obtained from healthy individual.

Alternatively information obtained from an individual at different time points of a defined time period can be used to track the performance of the heart of the individual such that changes in heart performance over this time period can be detected.

In any case, it will be appreciated that tracking heart performance over an extended time period is particularly advantageous in cases where an individual suffers from progressive heart diseases, since in these cases a change in heart performance typically dictates a change in medication or treatment regimen. Since prior art invasive monitoring methods cannot readily be used to track heart performance over an extended period of time, physicians oftentimes resort to non-invasive methods to track the heart performance of a patient. Due to inherent limitations non-invasive monitoring methods do not always provide the physician with accurate heart performance information and as such the use of such monitoring methods may result in suboptimal treatment regimens.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Example 1

Pulsatile Flow of Liquids in Arteries—Theoretical Considerations

Blood flow in the arteries is pulsatile. Blood is ejected from the left ventricle of the heart into the aorta, and the entire vascular system, in sharp pulses. The pulsatile nature of the flow manifests as sharp, periodic fluctuations in the instantaneous blood pressure, as well as in the flow velocity along the arteries.

The purpose of the following series of experiments is to demonstrate how one can determine the rate of flow in a blood vessel such as an artery from instantaneous pressure measurements at various points along the length of the artery.

In these experiments a coronary artery was modeled by a flexible latex tube, and the properties of a pulsatile flow of water through the tube were studied using pressure sensors mounted within the tube.

The theory of pulsatile flow of a liquid or a gas through a pipe is essentially one of acoustics, with certain modifications.

Let the radius of the pipe be a, and let the liquid be characterized by a density $\rho$ and a free-field sound velocity $c_0$. Using the cylindrical coordinate system (x,r,θ), where x denotes the direction along the pipe length, and (r,θ) lie in the pipe cross-section, the flow is characterized everywhere by a time-and-position dependent pressure P(r,θ,x,t) and the particle velocity (not to be confused with sound velocity) is $\vec{v}$(r,θ,x,t).

Interest is given herein almost exclusively to cases wherein the diameter of the pipe is much smaller than any acoustic wavelength possible in the medium. This means that, in all but a few cases, any pressure variations in the (r,θ) plane will equilibrate very rapidly, so that the pressure can be considered to be constant in that plane. Consequently, in this approximation the pressure is a function of x only, and the velocity has only one significant component, $\vec{v}$x. In the following the x subscript is therefore dropped, and the particle velocity in the x direction is simply denoted by v.

A further approximation which may be made is that v is also constant along the (r,θ) plane. This approximation is usually violated only very near the vessel boundaries, where viscous effects give rise to a dissipative boundary layer. This layer is however very thin, and so can be neglected when dealing with large (a few mm in diameter or more) vessels such as an artery.

The propagation of a pressure pulse along a blood vessel is described by means of two equations. The first is the continuity, or preservation of mass, equation, while the second is Newton's second law of mechanics (equality of forces). In free space, and in a perfectly rigid pipe, the result is the acoustic wave equation, which describes propagation of sound waves with a constant velocity $c_0$, $$\frac{\partial^2 P(x,t)}{\partial x^2} - \frac{1}{c_0^2}\frac{\partial^2 P(x,t)}{\partial t^2} = 0$$

where P is the pressure, x is the displacement and t is the time.

In the case of a blood vessel such as an artery, the propagation of pressure pulses is monitored in a pipe which is elastic (as opposed to rigid). In such a case, there are two additional effects which come into play. The first is the fact that an increase in fluid pressure causes an expansion of the pipe walls. This translates into an effective compressibility of the fluid which is much greater than the bulk value. The second effect is the inclusion of inertial forces resulting from the concomitant acceleration of the pipe walls, which are not massless, as they expand and contract. Both these effects taken together significantly modify the speed of sound inside the pipe. Thus the speed of sound inside a substantially flexible pipe is represented by:

$$c \approx \sqrt{\frac{Eh}{2a\rho}}\left[1 - \left(\frac{\omega}{\omega_c}\right)^2\right], \quad \omega_c = \sqrt{\frac{E}{\rho_W a^2}}$$

where ρ, E, h are the density, elastic modulus and thickness of the pipe walls, respectively, and $\rho_W$ is the density of the liquid.

One can see that the speed of sound is frequency-dependent, i.e., the medium is dispersive. However, this is significant only around and above the cutoff frequency $\omega_c$, which is usually above the frequency range of interest here. For low frequencies, consequently, one has an almost non-dispersive medium with a sound speed much lower than that of the bulk liquid. For example, while the free-field sound velocity in water is approximately 1500 m/sec, the velocity in a typical latex rubber tube which was used for modeling a blood vessel is only 16 m/sec, and in the arterial system it is even lower, about 3–5 m/sec.

By including two closely spaced pressure sensors in the tube it is possible to measure not only the pressure, but also the pressure gradient. This is a useful thing to do, for the following reason. Consider a section of length dx of liquid inside the pipe. The mass of this section is given by m=ρAdx, the mean acceleration is given by ∂<v>/∂t, and the longitudinal force operating on this section of pipe is F=A [P(x,t)−P(x+dx,t)]≈−A(∂P/dx)dx. These quantities are related via Newton's second law, F=m<v̇>, or, $$\langle v(t) - v(t_0)\rangle \approx \frac{1}{\rho}\int_0^t [P(x,t') - P(x+dx,t')]dt'$$

wherein the left term in the equation is the mean velocity difference between time point t and time point $t_0$.

Consequently, by measuring the instantaneous pressure at two nearby points one can calculate the mean flow rate across these two sensors, since the density ρ is known.

Further detail relating to the use of a pair of pressure sensors to measure pulsatile flow are provided in U.S. patent application Ser. No. 09/161,658

Example 2

Acoustic Transducer

FIGS. 1a, 1b and 2a–2e illustrate a preferred embodiment of a transducer element utilizable by one embodiment of the system of the present invention. As shown in the figures, the transducer element 1 includes at least one cell member 3 including a cavity 4 etched into a substrate and covered by a substantially flexible piezoelectric layer 2. Attached to piezoelectric layer 2 are an upper electrode 8 and a lower electrode 6, the electrodes for connection to an electronic circuit. The substrate is preferably made of an electrical conducting layer 11 disposed on an electrically insulating layer 12, such that cavity 4 is etched substantially through the thickness of electrically conducting layer 11.

Electrically conducting layer 11 is preferably made of copper and insulating layer 12 is preferably made of a polymer such as polyimide. Conventional copper-plated polymer laminate such as KAPTON™ sheets may be used for the production of transducer element 1. Commercially available laminates such as NOVACLAD™ may be used. Alternatively, the substrate may include a silicon layer, or any other suitable material. Alternatively, layer 11 is made of a non-conductive material such as PYRALIN™.

Preferably, cavity 4 is etched into the substrate by using conventional printed-circuit photolithography methods. Alternatively, cavity 4 may be etched into the substrate by using VLSI/micro-machining technology or any other suitable technology.

Piezoelectric layer 2 may be made of PVDF or a copolymer thereof. Alternatively, piezoelectric layer 2 is made of a substantially flexible piezoceramic. Preferably, piezoelectric layer 2 is a poled PVDF sheet having a thickness of about 9–28 μm. Preferably, the thickness and radius of flexible layer 2, as well as the pressure within cavity 4, are specifically selected so as to provide a predetermined resonant frequency. When using the embodiment of FIGS. 1a and 1b, the radius of layer 2 is defined by the radius of cavity 4.

By using a substantially flexible piezoelectric layer 2, the invention described in U.S. patent application Ser. No. 9/000,553 allows to provide a miniature transducer element whose resonant frequency is such that the acoustic wavelength is much larger than the extent of the transducer. This enables the transducer to be omnidirectional even at resonance, and further allows the use of relatively low frequency acoustic signals which do not suffer from significant attenuation in the surrounding medium.

Prior art designs of miniature transducers, however, rely on rigid piezoceramic usually operating in thickness mode. In such cases the resonant frequency relates to the size of the element and speed of sound in the piezoceramic, and is higher by several orders of magnitude.

The invention described in U.S. patent application Ser. No. 09/000,553 provides a transducer which is omnidirectional, i.e., insensitive to the direction of the impinging acoustic rays, thereby substantially simplifying the transducer's operation relative to other resonant devices. Such a transducer element is thus suitable for application in confined or hidden locations, where the orientation of the transducer element cannot be ascertained in advance.

According to a specific embodiment, cavity 4 features a circular or hexagonal shape with radius of about 200 $\mu$m. Electrically conducting layer 11 preferably has a thickness of about 15 $\mu$m. Cell member 3 is preferably etched completely through the thickness of electrically conducting layer 11. Electrically insulating layer 12 preferably features a thickness of about 50 $\mu$m. The precise dimensions of the various elements of a transducer element according to the invention described in U.S. patent application Ser. No. 09/000,553 may be specifically tailored according to the requirements of the specific application.

Cavity 4 preferably includes a gas such as air. The pressure of gas within cavity 4 may be specifically selected so as to predetermine the sensitivity and ruggedness of the transducer as well as the resonant frequency of layer 2.

Figure 2A:
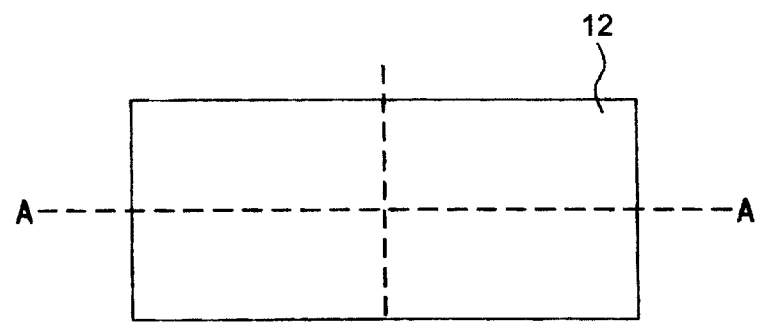
FIG. 2a is a cross section of a transducer element according to the present invention taken along line C—C in FIG. 1a (prior art, described in PCT/US98/27669)
Figure 2B:
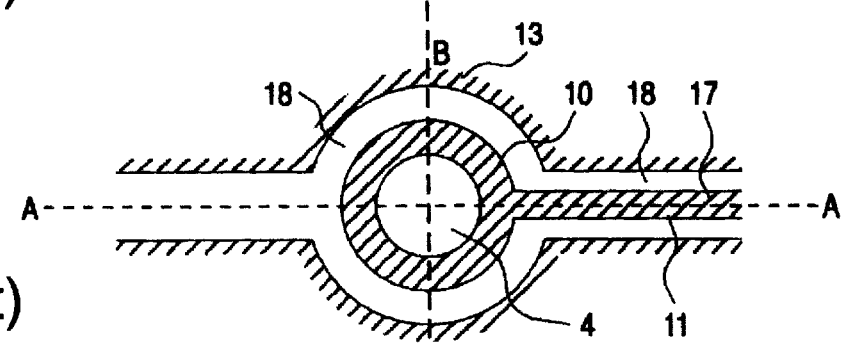
FIG. 2b is a cross section of a transducer element according to the present invention taken along line D—D in FIG. 1a (prior art, described in PCT/US98/27669)

As shown in FIG. 2b, an insulating chamber 18 is etched into the substrate, preferably through the thickness of conducting layer 11, so as to insulate the transducer element from other portions of the substrate which may include other electrical components such as other transducer elements etched into the substrate. According to a specific embodiment, the width of insulating chamber 18 is about 100 $\mu$m. As shown, insulating chamber 18 is etched into the substrate so as to form a wall 10 of a predetermined thickness enclosing cavity 4, and a conducting line 17 integrally made with wall 10 for connecting the transducer element to another electronic component preferably etched into the same substrate, or to an external electronic circuit.

Figure 1B:
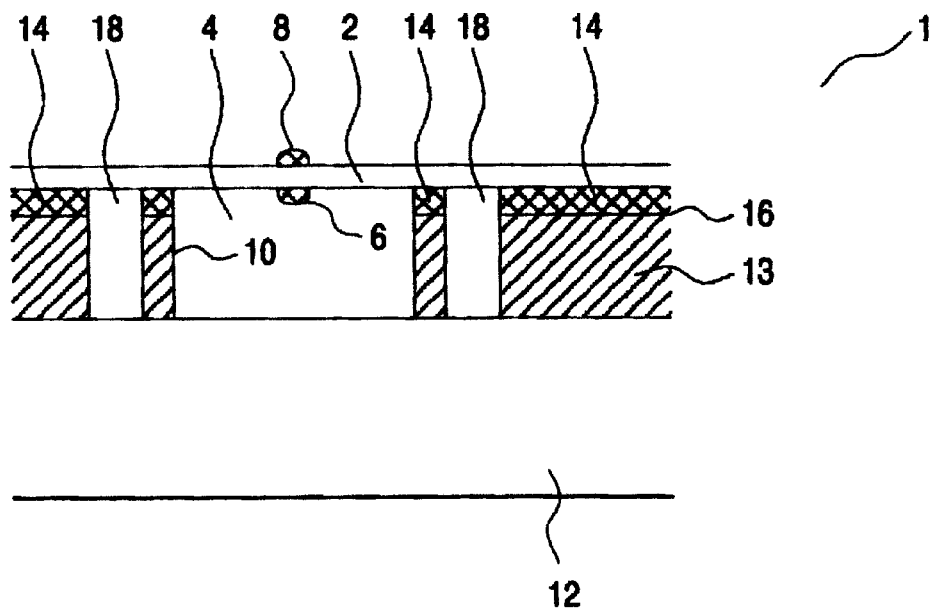
FIG. 1b is a longitudinal section of a transducer element according to the present invention taken along lines B—B in FIGS. 2a–2e (prior art, described in PCT/US98/27669)
Figure 2C:
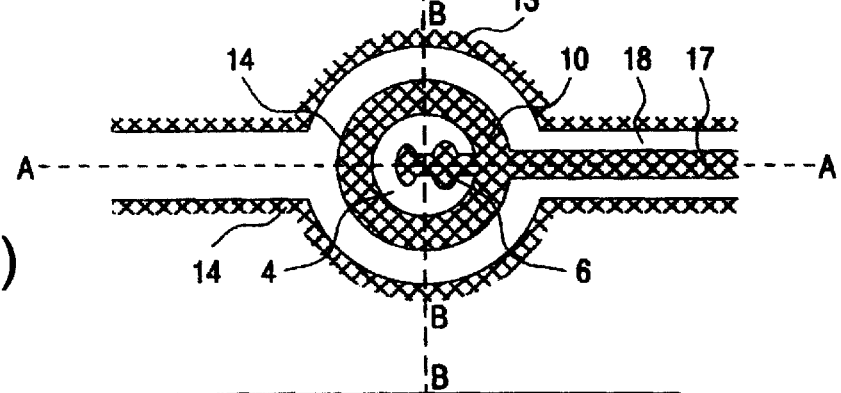
FIG. 2c is a cross section of a transducer element according to the present invention taken along line E—E in FIG. 1a (prior art, described in PCT/US98/27669)
Figure 2D:
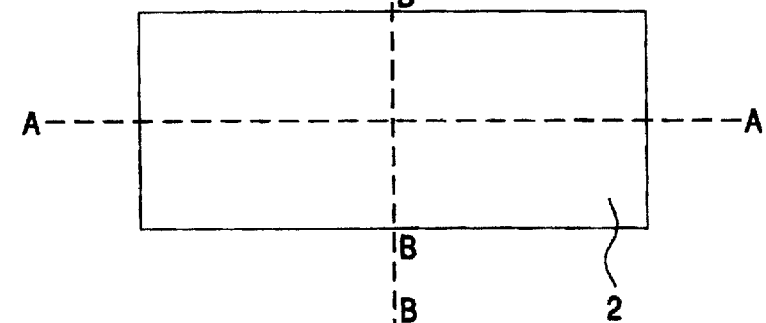
FIG. 2d is a cross section of a transducer element according to the present invention taken along line F—F in FIG. 1a (prior art, described in PCT/US98/27669)
Figure 2E:
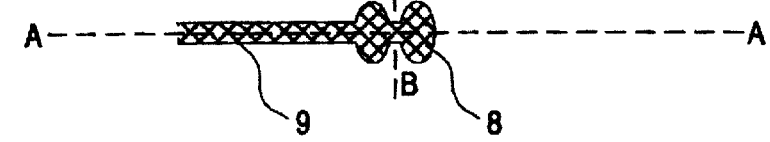
FIG. 2e is a cross section of a transducer element according to the present invention taken along line G—G in FIG. 1a (prior art, described in PCT/US98/27669)

As shown in FIGS. 1a and 1b, attached to piezoelectric layer 2 are upper electrode 8 and lower electrode 6. As shown in FIGS. 2c and 2e, upper electrode 8 and lower electrode 6 are preferably precisely shaped, so as to cover a predetermined area of piezoelectric layer 2. Electrodes 6 and 8 may be deposited on the upper and lower surfaces of piezoelectric membrane 2, respectively, by using various methods such as vacuum deposition, mask etching, painting, and the like.

As shown in FIG. 1a, lower electrode 6 is preferably made as an integral part of a substantially thin electrically conducting layer 14 disposed on electrically conducting layer 11. Preferably, electrically conducting layer 14 is made of a Nickel-Copper alloy and is attached to electrically conducting layer 11 by means of a sealing connection 16. Sealing connection 16 may be made of indium. According to a preferred configuration, sealing connection 16 may feature a thickness of about 10 $\mu$m, such that the overall height of wall 10 of cavity 4 is about 20–25 $\mu$m.

As shown in FIG. 2c, electrically conducting layer 14 covers the various portions of conducting layer 11, including wall 10 and conducting line 17. The portion of conducting layer 14 covering conducting line 17 is for connection to an electronic component, as further detailed hereinunder.

According to a preferred embodiment, electrodes 6 and 8 are specifically shaped to include the most energy-productive region of piezoelectric layer 2, so as to provide maximal response of the transducer while optimizing the electrode area, and therefore the cell capacitance, thereby maximizing a selected parameter such as voltage sensitivity, current sensitivity, or power sensitivity of the transducer element.

The vertical displacement of piezoelectric layer 2, $\Psi$, resulting from a monochromatic excitation at angular frequency $\omega$ is modeled using the standard equation for thin plates:

$$(\nabla^2 - \gamma^2)(\nabla^2 + \gamma^2)\Psi - \frac{3(1-v^2)}{2Qh^3}P + \frac{3iZ\omega(1-v^2)}{2Qh^3}\Psi = 0$$

wherein Q is the Young's modulus representing the elasticity of layer 2; h the half-thickness of layer 2; v is the Poisson ratio for layer 2; $\gamma$ is the effective wavenumber in the layer given by: $\gamma^4 = 3\rho(1-v^2)\omega^2/Qh^2$, wherein $\rho$ is the density of layer 2 and $\omega$ is the angular frequency of the applied pressure (wherein the applied pressure may include the acoustic pressure, the static pressure differential across layer 2 and any other pressure the transducer comes across); Z is the mechanical impedance resulting from the coupling of layer 2 to both external and internal media of cavity 4, wherein the internal medium is preferably air and the external medium is preferably fluid; P is the acoustic pressure applied to layer 2, and $\overline{\Omega}$ represents the average vertical displacement of layer 2.

When chamber 4 is circular, the solution (given for a single frequency component $\omega$) representing the dynamic displacement of a circular layer 2 having a predetermined radius a, expressed in polar coordinates, is:

$$\Psi(r,\varphi) = \frac{I_1(\gamma a)[J_0(\gamma r) - J_0(\gamma a)] + J_1(\gamma a)[I_0(\gamma r) - I_0(\gamma a)]}{2h\rho\omega^2 L_0(\gamma a) + i\omega Z L_2(\gamma a)} P$$

$$L_0(z) = I_0(z)J_1(z) + J_0(z)I_1(z), \quad L_2(z) = J_2(z)I_1(z) - I_2(z)J_1(z)$$

$$Z = \frac{P_A}{i\omega H_A} + i\left[\frac{4}{3\pi} + \frac{1}{6}\right]\omega\rho_W a$$

wherein $\Psi(r,\phi)$ is time-dependent and represents the displacement of a selected point located on circular layer 2, the specific location of which is given by radius r and angle $\phi$; J and I are the normal and modified Bessel functions of the first kind, respectively; $P_A$, $H_A$ are the air pressure is within cavity 4 and the height of chamber 4, respectively; and $\rho_W$, is the density of the fluid external to cavity 4.

The first term of the impedance Z relates to the stiffness resulting from compression of air within cavity 4, and the second term of Z relates to the mass added by the fluid boundary layer. An additional term of the impedance Z relating to the radiated acoustic energy is substantially negligible in this example.

The charge collected between electrodes 6 and 8 per unit area is obtained by evaluating the strains in layer 2 resulting from the displacements, and multiplying by the pertinent off-diagonal elements of the zoelectric strain coefficient tensor, $e_{31}$, $e_{32}$, as follows:

$$Q(r, \varphi, t) = \left(e_{31}\left(\frac{\partial \Psi}{\partial x}\right)\right)^2 + \left(e_{32}\left(\frac{\partial \Psi}{\partial y}\right)\right)^2$$

wherein $Q(r,\phi,t)$ represents the charge density at a selected point located on circular layer 2, the specific location of which is given by radius r and angle $\phi$; x is the stretch direction of piezoelectric layer 2; y is the transverse direction (the direction perpendicular to the stretch direction) of layer 2; $e_{31}$, $e_{32}$ are off-diagonal elements of the piezoelectric strain coefficient tensor representing the charge accumulated at a selected point on layer 2 due to a given strain along the x and y directions, respectively, which coefficients being substantially dissimilar when using a PVDF layer. $\Psi$ is the displacement of layer 2, taken as the sum of the displacement for a given acoustic pressure P at frequency f, and the static displacement resulting from the pressure differential between the interior and exterior of cavity 4, which displacements being extractable from the equations given above.

The total charge accumulated between electrodes 6 and 8 is obtained by integrating $Q(r,\phi,t)$ over the entire area S of the electrode:

$$Q = \int_S Q(r, \varphi, t) \, d\vec{x}$$

The capacitance C of piezoelectric layer 2 is given by:

$$C = \frac{\varepsilon}{2h} \int_S d\vec{x},$$

wherein $\varepsilon$ is the dielectric constant of piezoelectric layer 2; and 2h is the thickness of piezoelectric layer 2.

Accordingly, the voltage, current and power responses of piezoelectric layer 2 are evaluated as follows:

$$V = \frac{2h \int_S Q(r, \varphi, t) d\vec{x}}{\varepsilon \int_S d\vec{x}},$$

$$I = 2i\omega \int_S Q(r, \varphi, t) \, d\vec{x},$$

$$W = \frac{4ih \left[\int_S Q(r, \varphi, t) d\vec{x}\right]^2}{\varepsilon \int_S d\vec{x}}$$

The DC components of Q are usually removed prior to the evaluation, since the DC currents are usually filtered out. The values of Q given above represent peak values of the AC components of Q, and should be modified accordingly, so as to obtain other required values such as RMS values.

According to the above, the electrical output of the transducer expressed in terms of voltage, current and power responses depend on the AC components of Q, and on the shape S of the electrodes. Further, as can be seen from the above equations, the voltage response of the transducer may be substantially maximized by minimizing the area of the electrode. The current response, however, may be substantially maximized by maximizing the area of the electrode.

Figure 3:
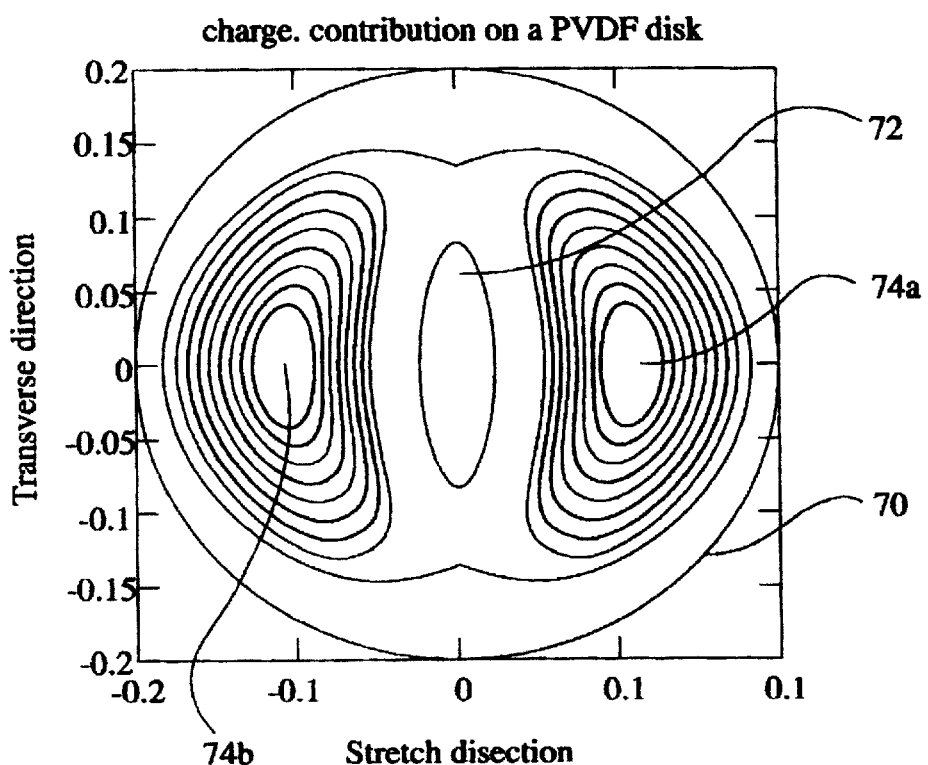
FIG. 3 shows the distribution of charge density across a piezoelectric layer of a transducer element resulting from the application of a constant pressure over the entire surface of the layer (prior art, described in PCT/US98/27669)
Figure 4A:
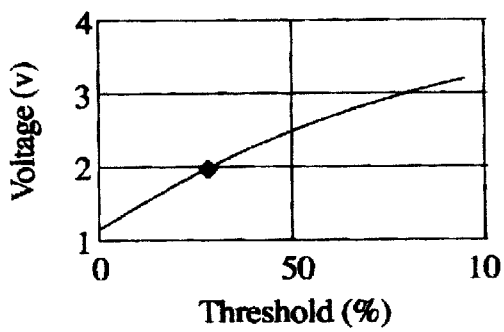
FIG. 4 shows the results of optimization performed for the power response of a transducer according to the present invention (prior art, described in PCT/US98/27669)
Figure 4C:
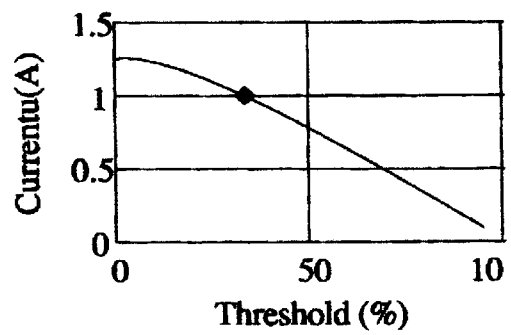
Figure 4B:
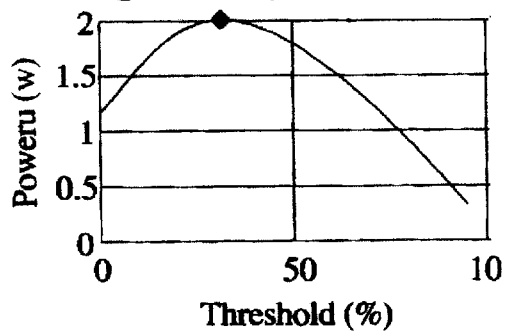
Figure 4D:
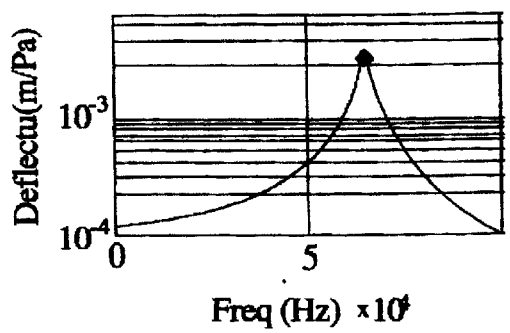

FIG. 3 shows the distribution of charge density on a circular piezoelectric layer 2 obtained as a result of pressure (acoustic and hydrostatic) applied uniformly over the entire area of layer 2, wherein specific locations on layer 2 are herein defined by using Cartesian coordinates including the stretch direction (x direction) and the transverse direction (y direction) of layer 2. It can be seen that distinct locations on layer 2 contribute differently to the charge density. The charge density vanishes at the external periphery 70 and at the center 72 of layer 2 due to minimal deformation of these portions. The charge density is maximal at two cores 74a and 74b located symmetrically on each side of center 72 due to maximal strains (in the stretch direction) of these portions.

A preferred strategy for optimizing the electrical responses of the transducer is to shape the electrode by selecting the areas contributing at least a selected threshold percentage of the maximal charge density, wherein the threshold value is the parameter to be optimized. A threshold value of 0% relates to an electrode covering the entire area of layer 2.

FIG. 4 shows the results of an optimization performed for the power response of a transducer having a layer 2 of a predetermined area. As shown in the Figure, the threshold value which provides an optimal power response is about 30% (graph b). Accordingly, an electrode which covers only the portions of layer 2 contributing at least 30% of the maximal charge density yields a maximal power response. The pertinent voltage response obtained by such an electrode is higher by a factor of 2 relative to an electrode completely covering layer 2 (graph a). The current response obtained by such electrode is slightly lower relative to an electrode completely covering layer 2 (graph c). Further as shown in the Figure, the deflection of layer 2 is maximal when applying an acoustic signal at the resonant frequency of layer 2 (graph d).

Figure 5:
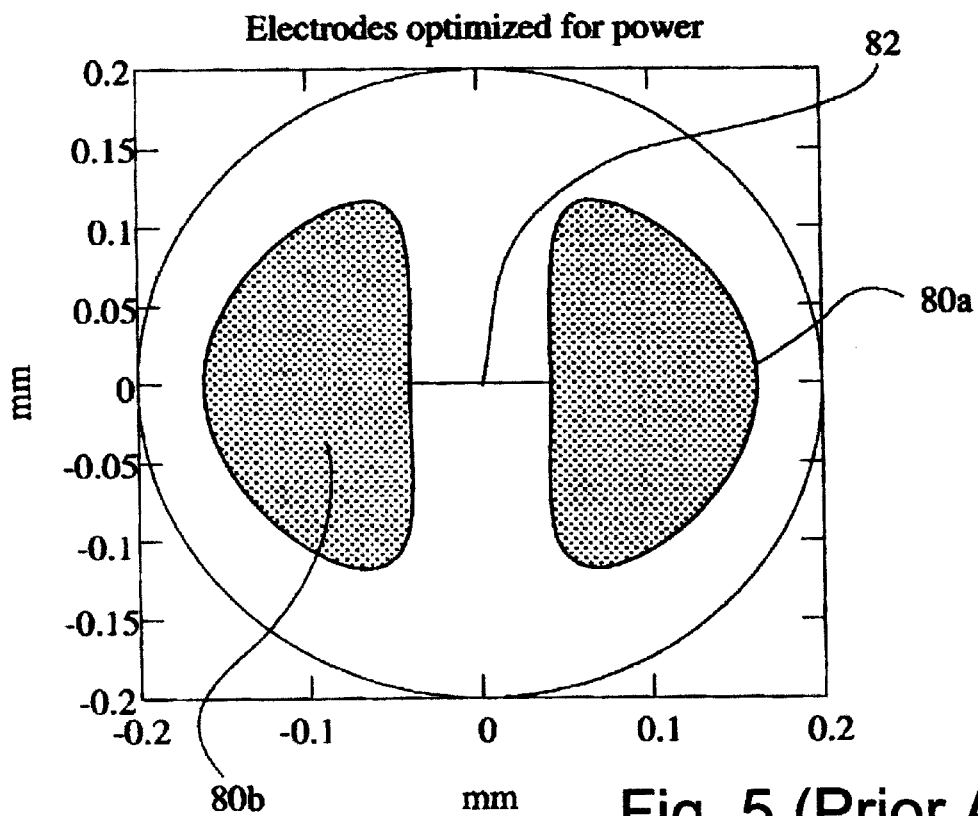
FIG. 5 shows a preferred electrode shape for maximizing the power response of a transducer according to the present invention (prior art, described in PCT/US98/27669)

A preferred electrode shape for maximizing the power response of the transducer is shown in FIG. 5, wherein the electrode includes two electrode portions 80a and 80b substantially covering the maximal charge density portions of layer 2, the electrode portions being interconnected by means of a connecting member 82 having a minimal area. Preferably, portions 80a and 80b cover the portions of layer 2 which yield at least a selected threshold (e.g. 30%) of the maximal charge density.

According to the present invention any other parameter may be optimized so as to determine the shape of electrodes 6 and 8. According to further features of the invention described in U.S. patent application Ser. No. 09/000,553, only one electrode (upper electrode 8 or lower electrode 6) may be shaped so as to provide maximal electrical response of the transducer, with the other electrode covering the entire area of layer 2. Since the charge is collected only at the portions of layer 2 received between upper electrode 8 and lower electrode 6, such configuration is operatively equivalent to a configuration including two shaped electrodes having identical shapes.

Figure 6:
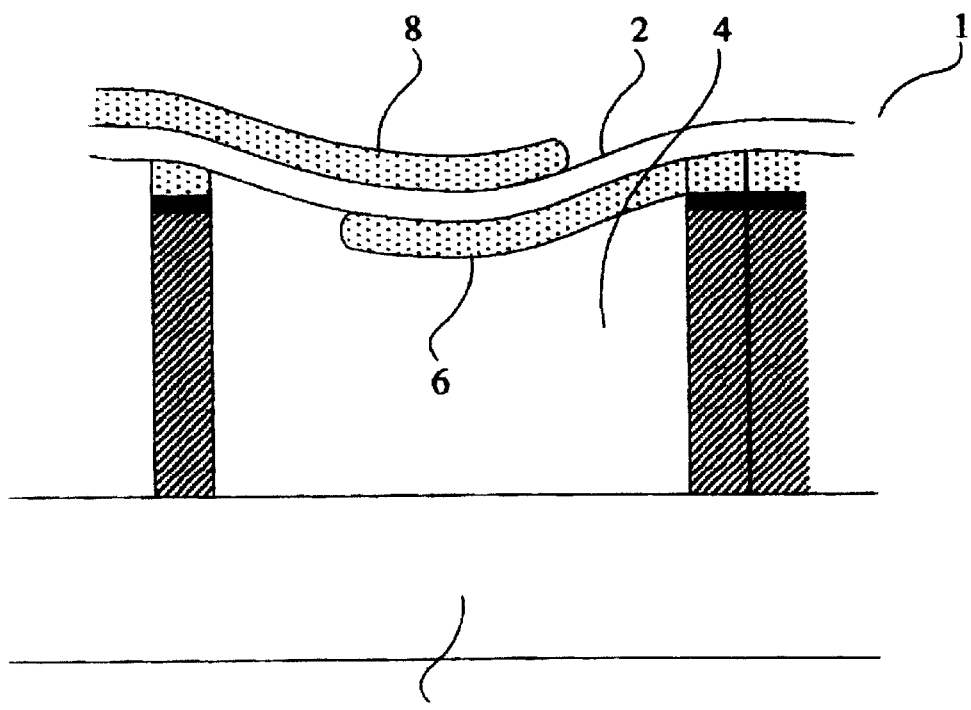
FIG. 6 is a longitudinal section of another embodiment of a transducer element according to the present invention capable of functioning as a transmitter (prior art, described in PCT/US98/27669)

Referring now to FIG. 6, according to another embodiment chamber 4 of transducer element 1 may contain gas of substantially low pressure, thereby conferring a substantially concave shape to piezoelectric membrane 2 at equilibrium. Such configuration enables to further increase the electrical response of the transducer by increasing the total charge obtained for a given displacement of layer 2. The total displacement in such an embodiment is given by: $\Psi = P_0 \Psi_{DC} + P \Psi_{AC} \cos \omega t$, wherein $P_0$ is the static pressure differential between the exterior and the interior of cavity 4; $\omega_{DC}$ is the displacement resulting from $P_0$; P is the amplitude of the acoustic pressure; and $\omega_{AC}$ is the displacement resulting from P.

Accordingly, the strain along the x direction includes three terms as follows:

$$S_{xx} = \left(\frac{\partial \Psi}{\partial x}\right)^2 = \left(P_0^2\left(\frac{\partial \Psi_{DC}}{\partial x}\right)\right)^2 + \left(P^2\left(\frac{\partial \Psi_{AC}}{\partial x}\right)\right)^2 \cos^2\omega t + 2P_0 P \frac{\partial \Psi_{DC}}{\partial x} \frac{\partial \Psi_{AC}}{\partial x} \cos\omega t$$

wherein the DC component is usually filtered out.

Thus, by decreasing the pressure of the medium (preferably air) within cavity 4 relative to the pressure of the external medium (preferably fluid), the value of $P_O$ is increased, thereby increasing the value of the third term of the above equation.

Such embodiment makes it possible to increase the charge output of layer 2 for a given displacement, thereby increasing the voltage, current and power responses of the transducer without having to increase the acoustic pressure P. Furthermore, such embodiment enables to further miniaturize the transducer since the same electrical response may be obtained for smaller acoustic deflections. Such embodiment is substantially more robust mechanically and therefore more durable than the embodiment shown in FIGS. 1a and 1b. Such further miniaturization of the transducer enables to use higher resonance frequencies relative to the embodiment shown in FIGS. 1a and 1b.

Preferably, a transducer element 1 according to the invention described in U.S. patent application Ser. No. 09/000,553 is fabricated by using technologies which are in wide use in the microelectronics industry, so as to allow integration thereof with other conventional electronic components as further detailed hereinunder. When the transducer element includes a substrate such as Copper-polymer laminate or silicon, a variety of conventional electronic components may be fabricated onto the same substrate.

According to a preferred embodiment, a plurality of cavities 4 may be etched into a single substrate 12 and covered by a single piezoelectric layer 2, so as to provide a transducer element including a matrix of transducing cell members 3, thereby providing a larger energy collecting area of predetermined dimensions, while still retaining the advantage of miniature individual transducing cell members 3. When using such configuration, the transducing cell members 3 may be electrically interconnected in parallel or serial connections, or combinations thereof, so as to tailor the voltage and current response of the transducer. Parallel connections are preferably used so as to increase the current output while serial connections are preferably used so as to increase the voltage output of the transducer.

Furthermore, piezoelectric layer 2 may be completely depolarized and then repolarized at specific regions thereof, so as to provide a predetermined polarity to each of the transducing cell members 3. Such configuration enables to reduce the complexity of interconnections between cell members 3.

A transducer element according to the invention described in U.S. patent application Ser. No. 09/000,553 may be further used as a transmitter for transmitting information to a remote receiver by modulating the reflection of an external impinging acoustic wave arrived from a remote transmitter.

Referring to FIG. 6, the transducer element shown may function as a transmitter element due to the asymmetric fluctuations of piezoelectric layer 2 with respect to positive and negative transient acoustic pressures obtained as a result of the pressure differential between the interior and exterior of cavity 4.

A transmitter element according to the present invention preferably modulates the reflection of an external impinging acoustic wave by means of a switching element connected thereto. The switching element encodes the information that is to be transmitted, such as the output of a sensor, thereby frequency modulating a reflected acoustic wave.

Such configuration requires very little expenditure of energy from the transmitting module itself, since the acoustic wave that is received is externally generated, such that the only energy required for transmission is the energy of modulation.

Specifically, the reflected acoustic signal is modulated by switching the switching element according to the frequency of a message electric signal arriving from another electronic component such as a sensor, so as to controllably change the mechanical impedance of layer 2 according to the frequency of the message signal.

Preferably, a specific array of electrodes connected to a single cell member or alternatively to a plurality of cell members are used, so as to control the mechanical impedance of layer 2.

Figure 7A:
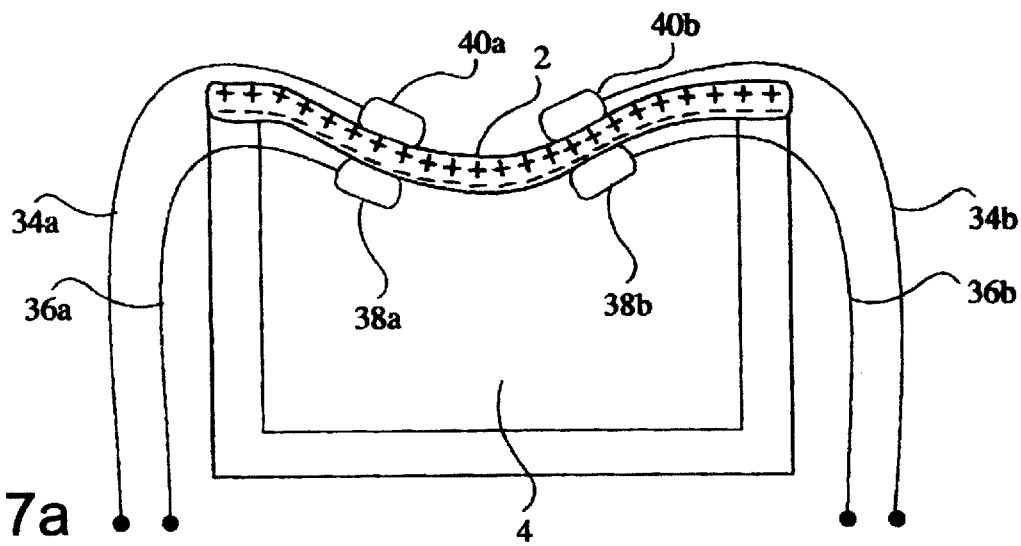
FIG. 7a–7f are schematic views of possible configurations of transmitters according to the present invention including parallel and anti-parallel electrical connections for controllably changing the mechanical impedance of the piezoelectric layer (prior art, described in PCT/US98/27669)

FIGS. 7a–7g illustrate possible configurations for controllably change the impedance of layer 2 of a transmitter element. Referring to FIG. 7a, a transmitter element according to the invention described in U.S. patent application Ser. No. 09/000,553 may include a first and second pairs of electrodes, the first pair including an upper electrode 40a and a lower electrode 38a, and the second pair including an upper electrode 40b and a lower electrode 38b. Electrodes 38a, 38b, 40a and 40b are electrically connected to an electrical circuit by means of conducting lines 36a, 36b, 34a and 34b, respectively, the electrical circuit including a switching element (not shown), so as to alternately change the electrical connections of conducting lines 36a, 36b, 34a and 34b.

Preferably, the switching element switches between a parallel connection and an anti-parallel connection of the electrodes. A parallel connection decreases the mechanical impedance of layer 2, wherein an anti-parallel connection increases the mechanical impedance of layer 2. An anti-parallel connection may be obtained by interconnecting line 34a to 36b and line 34b to 36a. A parallel connection may be obtained by connecting line 34a to 34b and line 36a to 36b. Preferably, the switching frequency equals the frequency of a message signal arriving from an electrical component such as a sensor as further detailed hereinunder.

Figure 7B:
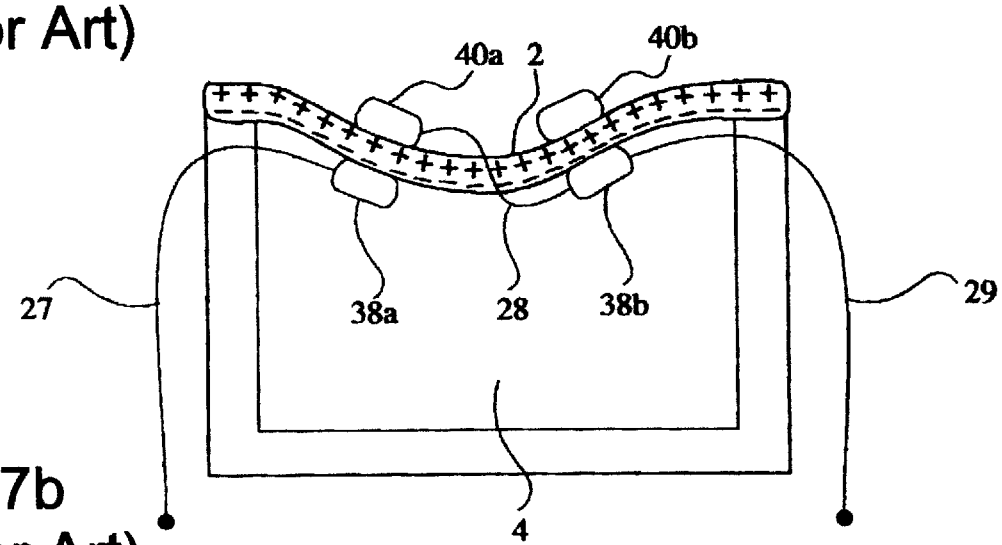

According to another embodiment shown in FIG. 7b, upper electrode 40a is connected to lower electrode 38b by means of a conducting line 28, and electrodes 38a and 40b are connected to an electrical circuit by means of conducting lines 27 and 29, respectively, wherein the electrical circuit further includes a switching element. Such configuration provides an anti-parallel connection of the electrodes, wherein the switching element functions as an on/off switch, thereby alternately increasing the mechanical impedance of layer 2.

Figure 7C:
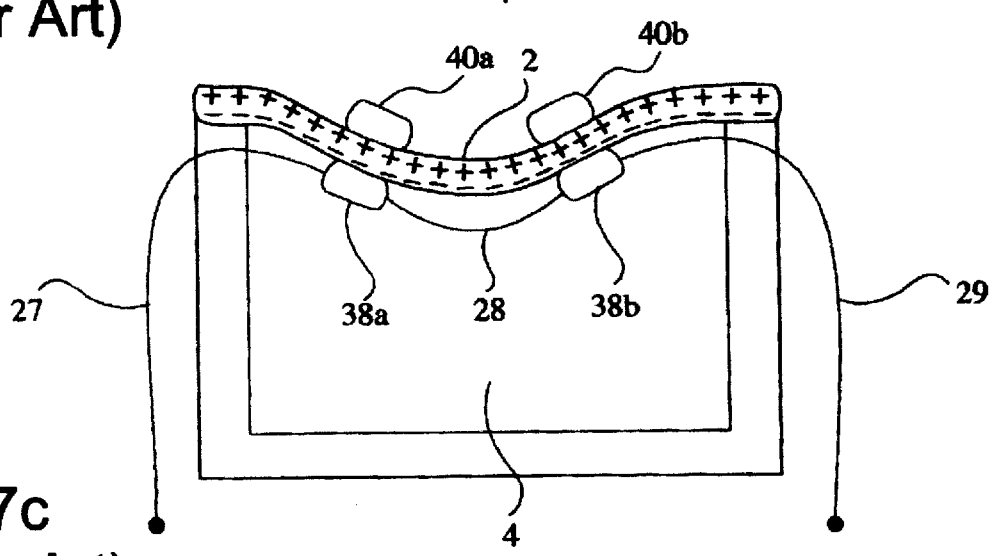

In order to reduce the complexity of the electrical connections, layer 2 may be depolarized and then repolarized at specific regions thereof. As shown in FIG. 7c, the polarity of the portion of layer 2 received between electrodes 40a and 38a is opposite to the polarity of the portion of layer 2 received between electrodes 40b and 38b. An anti-parallel connection is thus achieved by interconnecting electrodes 38a and 38b by means of a conducting line 28, and providing conducting lines 27 and 29 connected to electrodes 40a and 40b, respectively, the conducting lines for connection to an electrical circuit including a switching element.

According to another embodiment, the transmitting element includes a plurality of transducing cell members, such that the mechanical impedance of layer 2 controllably changed by appropriately interconnecting the cell members.

Figure 7D:
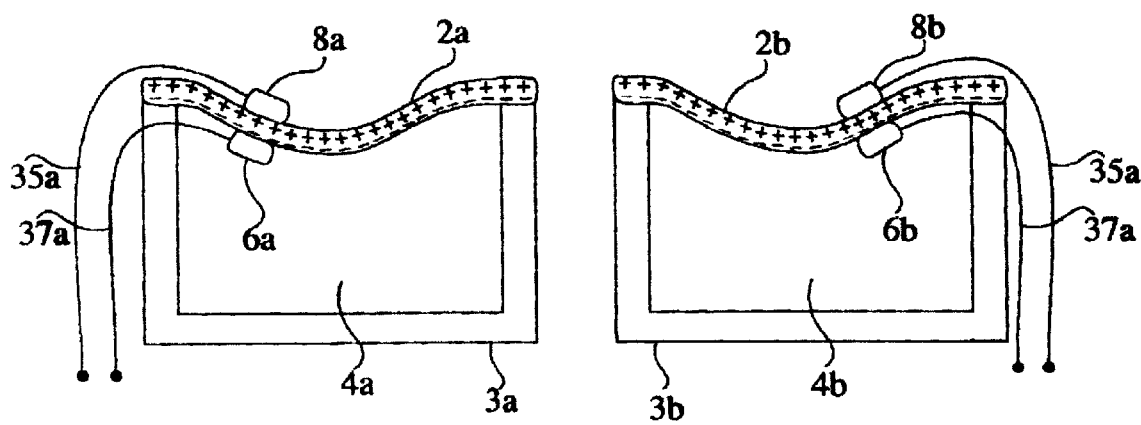

As shown in FIG. 7d, a first transducing cell member 3a including a layer 2a and a cavity 4a, and a second transducing cell member 3b including a layer 2b and a cavity 4b are preferably contained within the same substrate; and layers 2a and 2b are preferably integrally made. A first pair of electrodes including electrodes 6a and 8a is attached to layer 2, and a second pair of electrode including electrodes 6b and 8b is attached to layer 2b. Electrodes 6a, 8a, 6b and 8b are electrically connected to an electrical circuit by means of conducting lines 37a, 35a, 37b and 35b, respectively, the electrical circuit including a switching element, so as to alternately switch the electrical connections of conducting lines 37a, 35a, 37b and 35b, so as to alternately provide parallel and anti-parallel connections, substantially as described for FIG. 7a, thereby alternately decreasing and increasing the mechanical impedance of layers 2a and 2b.

Figure 7E:
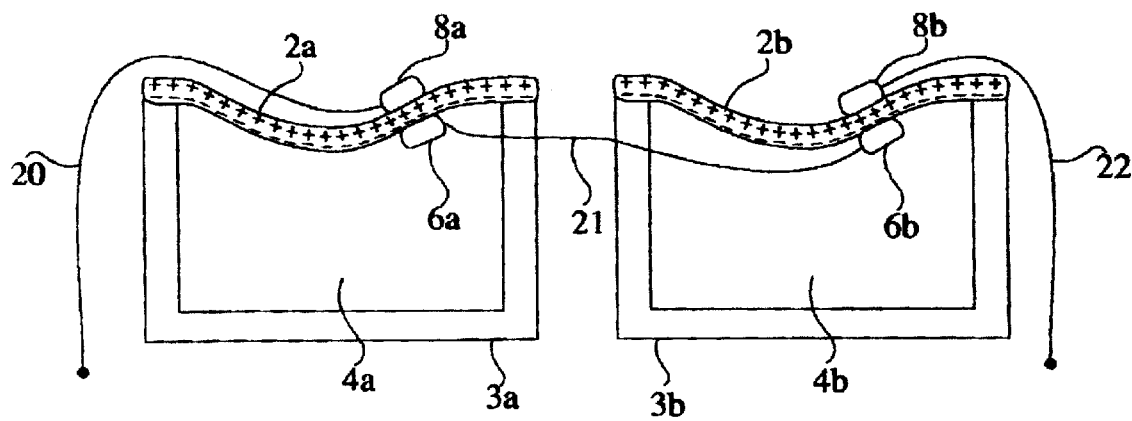

FIG. 7e illustrates another embodiment, wherein the first and second transducing cell members are interconnected by means of an anti-parallel connection. As shown in the Figure, the polarity of layer 2a is opposite to the polarity of layer 2b, so as to reduce the complexity of the electrical connections between cell members 3a and 3b. Thus, electrode 6a is connected to electrode 6b by means of a conducting line 21, and electrodes 8a and 8b are provided with conducting lines 20 and 22, respectively, for connection to an electrical circuit which includes a switching element, wherein the switching element preferably functions as an on/off switch, so as to alternately increase the mechanical impedance of layers 2a and 2b.

Figure 7F:
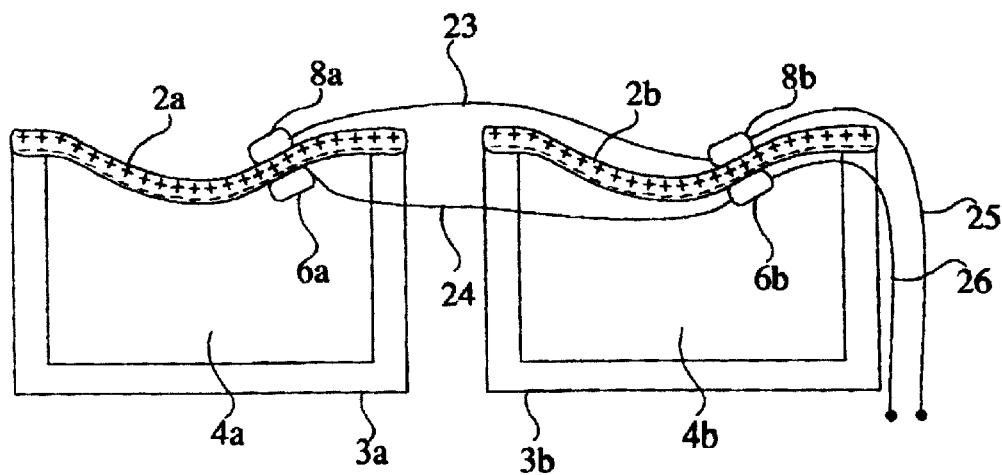

FIG. 7f shows another embodiment, wherein the first and second transducing cell members are interconnected by means of a parallel connection. As shown, electrodes 6a and 6b are interconnected by means of conducting line 24, electrodes 8a and 8b are interconnected by means of conducting line 23, and electrodes 6b and 8b are provided with conducting lines 26 and 25, respectively, the conducting lines for connection to an electrical circuit including a switching element. The switching element preferably functions as an on/off switch for alternately decreasing and increasing the mechanical impedance of layers 2a and 2b.

Figure 8:
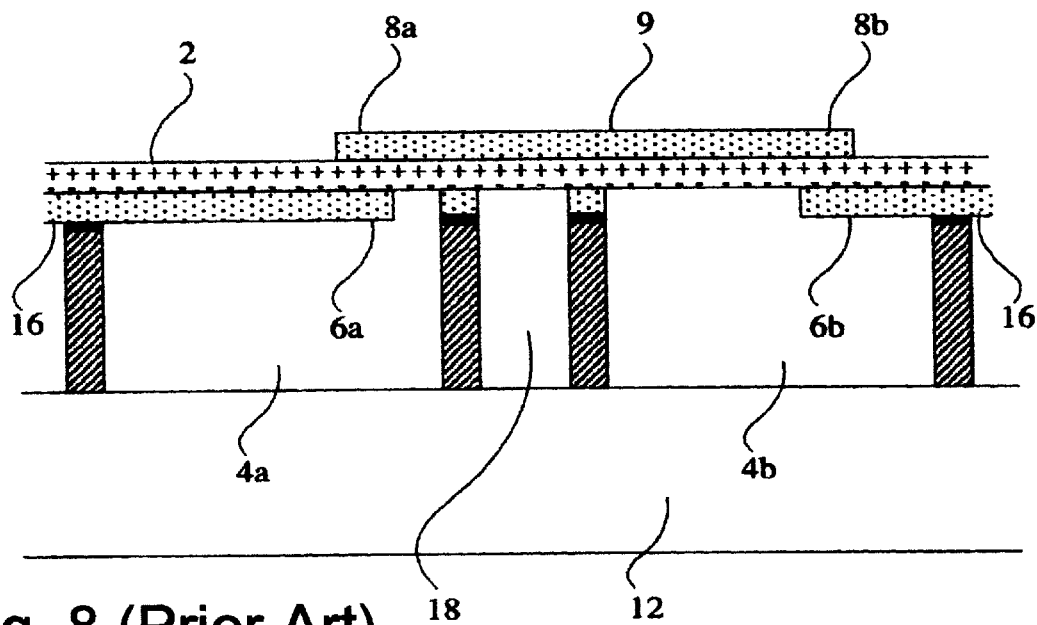
FIG. 8 is a longitudinal section of a transmitter element according to the present invention including an anti-parallel electrical connection (prior art, described in PCT/US98/27669)

FIG. 8 shows a possible configuration of two transducing cell members etched onto the same substrate and interconnected by means of an anti-parallel connection. As shown in the Figure, the transducing cell members are covered by a common piezoelectric layer 2, wherein the polarity of the portion of layer 2 received between electrodes 6a and 8a is opposite to the polarity of the portion of layer 2 received between electrodes 6b and 8b. Electrodes 8a and 8b are bonded by means of a conducting line 9, and electrodes 6a and 6b are provided with conducting lines 16 for connection to an electrical circuit.

Figure 9:
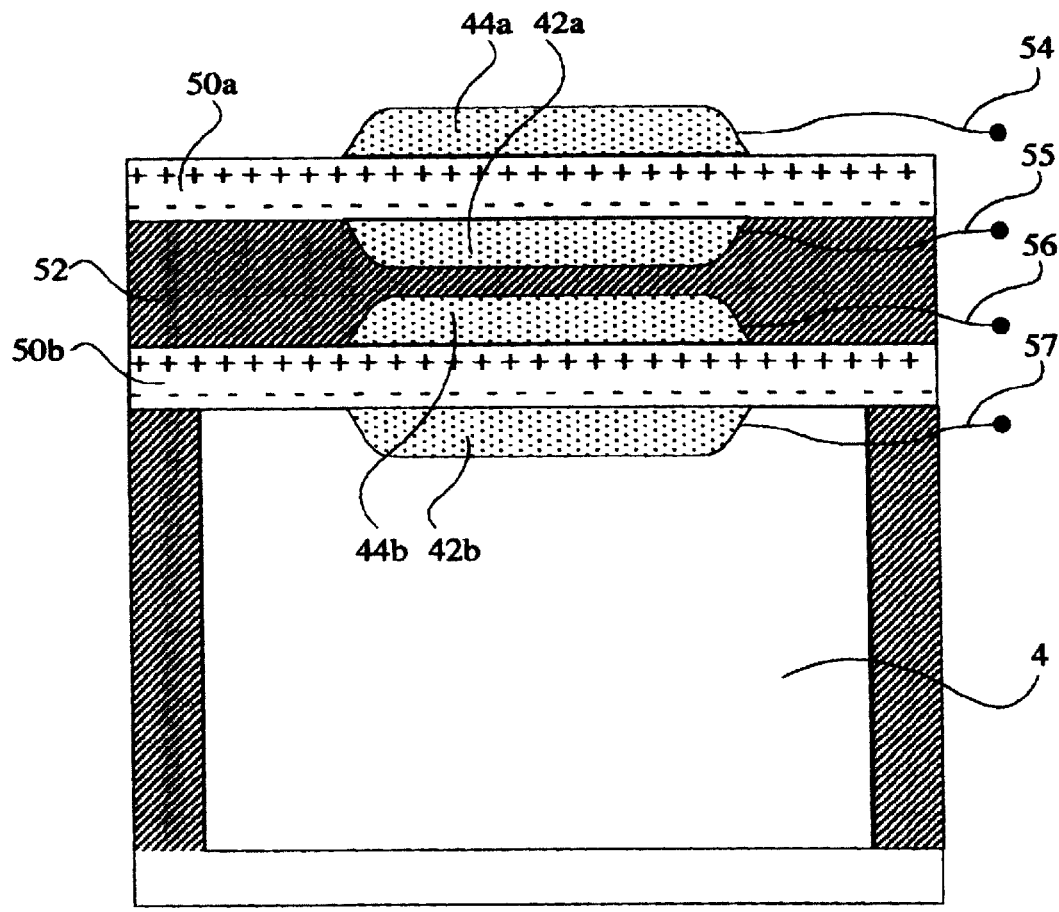
FIG. 9 is a longitudinal section of another embodiment of a transmitter element according to the present invention (prior art, described in PCT/US98/27669)

Another embodiment of a transmitter element according to the present invention is shown in FIG. 9. The transmitter element includes a transducing cell member having a cavity 4 covered by a first and second piezoelectric layers, 50a and 50b, preferably having opposite polarities. Preferably, layers 50a and 50b are interconnected by means of an insulating layer 52. Attached to layer 50a are upper and lower electrodes 44a and 42a, and attached to layer 50b are upper and lower electrodes 44b and 42b. Electrodes 44a, 42a, 44b and 42b are provided with conducting lines 54, 55, 56 and 57, respectively, for connection to an electrical circuit.

It will be appreciated that the above descriptions are intended only to serve as examples, and that many other embodiments are possible within the spirit and the scope of invention described in U.S. patent application Ser. No. 09/000,553.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications cited herein are incorporated by reference in their entirety.

What is claimed is:

1. An intrabody implantable system for long-term, real time monitoring of at least one parameter associated with heart performance, the system comprising:
   (a) a first sensor being implantable within a heart and being for collecting information pertaining to a pressure in a first cavity of the heart;
   (b) at least one additional sensor being implantable in a blood vessel supporting blood into or out of a second cavity of the heart, said at least one additional sensor being for collecting information pertaining to a pressure and a flow within said blood vessel; and
   (c) at least one device implantable in the body and being in data communication with said first sensor and said at least one additional sensor, said at least one device being for receiving said information pertaining to said pressure in the first cavity of the heart and said information pertaining to said pressure and said flow within said blood vessel and for relaying said information pertaining to said pressure in the first cavity of the heart and said information pertaining to said pressure and said flow within said blood vessel outside the body.

2. The system of claim 1, wherein said first cavity is a ventricle.

3. The system of claim 1, wherein said blood vessel is an artery.

4. The system of claim 3, wherein said artery is a pulmonary artery.

5. The system of claim 1, wherein said at least one additional sensor includes at least two pressure sensors being implantable in a spaced apart configuration within said blood vessel, said at least two pressure sensors being for collecting said information pertaining to said pressure and said flow within said blood vessel.

6. The system of claim 5, wherein said at least two pressure sensors are attached to or integrally formed with a stent assembly, said stent assembly being configured so as to be positionable within said blood vessel.

7. The system of claim 6, wherein said at least one device includes a plurality of devices and further wherein said stent assembly includes a device of said plurality of devices attached thereto and being in communication with each of said at least two pressure sensors.

8. The system of claim 1, further comprising an extracorporeal processing unit capable of receiving, processing and interpreting said information pertaining to said pressure in the first cavity of the heart and said information pertaining to said pressure and said flow within said blood vessel relayed outside the body by said at least one device.

9. The system of claim 1, wherein said first sensor is a pressure sensor and further wherein said information pertaining to said pressure in the first cavity of the heart pertains to both active and passive pressures within said first cavity.

10. The system of claim 1, wherein said at least one device includes at least one transducer for converting electric signal into a radiative signal.

11. The system of claim 10, wherein said radiative signal is selected from the group consisting of radio frequency, a magnetic field, an electric field and acoustic radiation.

12. The system of claim 10, wherein said at least one transducer is an acoustic transducer and further wherein said radiative signal is an acoustic signal.

13. The system of claim 10, wherein said transducer is a magnetic field transducer and further wherein said signal is a magnetic field signal.

14. The system of claim 1, further comprising at least one power source, said at least one power source being in electrical communication with said first sensor and said at least one additional sensor.

15. The system of claim 14, wherein said at least one power source is integrated into said at least one device.

16. The system of claim 14, wherein said at least one power source is selected from the group consisting of at least one energy containing power source and at least one energizeable power source.

17. The system of claim 16, wherein said at least one energizeable power source includes at least one transducer for converting a radiative energy into electric energy.

18. The system of claim 17, wherein said radiative energy is selected from the group consisting of radio frequency, a magnetic field, an electric field and acoustic radiation.

19. The system of claim 17, wherein said at least one transducer is an acoustic transducer and further wherein said radiative energy is an acoustic energy.

20. The system of claim 17, wherein said transducer is a magnetic field transducer and further wherein said radiative energy is a magnetic field.

21. The system of claim 1, wherein said at least additional sensor is attached to or integrally formed with a stent assembly, said stent assembly being configured so as to be positionable within said blood vessel.

22. The system of claim 21, wherein said at least one device includes a plurality of devices and further wherein said stent assembly includes a device of said plurality of devices attached thereto and being in communication with said at least one additional sensor.

23. A method of monitoring the heart performance of an individual, the method comprising the steps of:
(a) implanting within the patient's body:
 (i) a first sensor within a heart for collecting information pertaining to a pressure in a first cavity of the heart; and
 (ii) at least one additional sensor in an blood vessel supporting blood flow into or out of a second cavity of the heart, said at least one additional sensor being for collecting information pertaining to a pressure and a flow within said blood vessel;
(b) extracorporeally retrieving and processing said information collected by said first sensor and said information collected by said at least one additional sensor;
(c) interpreting said information resultant from step (b) so as to yield interpreted information pertaining to the heart performance of the patient; and
(d) if required, repeating steps (b) through (c) a predetermined number of times over a predetermined time period so as to enable monitoring the heart performance of the individual.

24. The method of claim 23, wherein said first cavity is a ventricle.

25. The system of claim 23, wherein said blood vessel is an artery.

26. The system of claim 25, wherein said artery is a pulmonary artery.

27. The method of claim 23, wherein said information pertaining to a pressure in the first cavity of the heart pertains to both active and passive pressures within said first cavity.

28. The method of claim 23, wherein said at least one additional sensor includes at least two pressure sensors being implantable in a spaced apart configuration within said blood vessel, said at least two pressure sensors being for collecting said information pertaining to said pressure and said flow within said blood vessel.

29. The method of claim 23, wherein said first sensor is a pressure sensor and further wherein said information pertaining to said pressure in the first cavity of the heart pertains to both active and passive pressures within said first cavity.

30. The method of claim 29, wherein said communication is selected from the group consisting of wire communication and wireless communication.

31. The method of claim 30, wherein said wireless communication is effected via radiative energy selected from the group consisting of radiofrequency energy, acoustic energy and magnetic field energy.

32. The method of claim 23, wherein said at least additional sensor is attached to or integrally formed with a stent assembly, said stent assembly being configured so as to be positionable within said blood vessel.

33. The method of claim 23, wherein said step of extracorporeally retrieving and processing said information collected by said first sensor and said information collected by said at least one additional sensor is effected by an extracorporeal processing unit being in communication with said first sensor and said at least one additional sensor.

34. A method of monitoring the heart performance of an individual, the method comprising the steps of:
(a) collecting and processing information pertaining to a pressure in a cavity of the heart;
(b) collecting and processing information pertaining to a pressure and a flow within an blood vessel supporting blood flow into or out of the heart;
(c) interpreting said information resultant from step (b) and said information resultant from step (c) so as to yield interpreted information pertaining to the heart performance of the patient; and
(d) repeating steps (b)–(d) a predetermined number of times over a predetermined time period so as to enable monitoring the heart performance of the individual.

* * * * *